United States Patent
Jennings et al.

(10) Patent No.: US 7,348,351 B2
(45) Date of Patent: Mar. 25, 2008

(54) SUBSTITUTED 3-ALKYL AND 3-ARYLALKYL 1H-INDOL-1YL ACETIC ACID DERIVATIVES AS INHIBITORS OF PLASMINOGEN ACTIVATOR INHIBITOR-1 (PAI-1)

(75) Inventors: Lee Dalton Jennings, Chestnut Ridge, NY (US); Scott Lee Kincaid, Middletown, NY (US)

(73) Assignee: Wyeth, Madison, NJ (US)

( * ) Notice: Subject to any disclaimer, the term of this patent is extended or adjusted under 35 U.S.C. 154(b) by 587 days.

(21) Appl. No.: 10/730,951

(22) Filed: Dec. 9, 2003

(65) Prior Publication Data
US 2004/0116488 A1    Jun. 17, 2004

Related U.S. Application Data

(60) Provisional application No. 60/432,330, filed on Dec. 10, 2002.

(51) Int. Cl.
*A61K 31/404*    (2006.01)
*C07D 209/04*    (2006.01)

(52) U.S. Cl. ............... 514/412; 548/452; 548/465
(58) Field of Classification Search ............ 548/452, 548/465; 514/412
See application file for complete search history.

(56) References Cited

U.S. PATENT DOCUMENTS

| | | | | |
|---|---|---|---|---|
| 3,026,325 A | 3/1962 | Heinzelman et al. | ...... | 548/496 |
| 3,476,770 A | 11/1969 | Scherrer | ...... | 548/494 |
| 3,557,143 A | 1/1971 | Bell | ...... | 548/516 |
| 3,843,683 A | 10/1974 | Bell | ...... | 548/493 |
| 4,478,819 A | 10/1984 | Hercelin et al. | ...... | 424/457 |
| 4,736,043 A | 4/1988 | Michel et al. | ...... | 548/492 |
| 4,851,406 A | 7/1989 | Mertens et al. | ...... | 514/217.04 |
| 5,164,372 A | 11/1992 | Matsuo et al. | ...... | 514/19 |
| 5,420,289 A | 5/1995 | Musser et al. | ...... | 548/159 |
| 5,482,960 A | 1/1996 | Berryman | ...... | 514/414 |
| 5,502,187 A | 3/1996 | Ayer et al. | ...... | 544/117 |
| 5,541,343 A | 7/1996 | Himmelsbach et al. | ...... | 514/424 |
| 5,612,360 A | 3/1997 | Boyd et al. | | |
| 5,859,044 A | 1/1999 | Dow et al. | ...... | 514/419 |
| 6,048,875 A | 4/2000 | De Nanteuil et al. | ...... | 514/314 |
| 6,110,963 A | 8/2000 | Malamas | ...... | 514/443 |
| 6,166,069 A | 12/2000 | Malamas et al. | ...... | 514/469 |
| 6,232,322 B1 | 5/2001 | Malamas et al. | ...... | 514/303 |
| 6,251,936 B1 | 6/2001 | Wrobel et al. | ...... | 514/443 |
| 6,302,837 B1 | 10/2001 | De Nanteuil et al. | ...... | 514/337 |
| 6,479,524 B1 | 11/2002 | Priepke et al. | ...... | 514/352 |
| 6,599,929 B2 | 7/2003 | Cho et al. | ...... | 514/415 |
| 6,787,556 B1 | 9/2004 | Hargreaves et al. | ...... | 514/331 |
| 6,800,645 B1 | 10/2004 | Cox et al. | ...... | 514/314 |
| 6,800,654 B2 | 10/2004 | Mayer et al. | ...... | 514/381 |
| 6,844,358 B2 | 1/2005 | Malamas et al. | ...... | 514/336 |
| 2003/0013732 A1 | 1/2003 | Elokdah | ...... | 514/301 |
| 2003/0018067 A1 | 1/2003 | Elokdah et al. | ...... | 514/469 |
| 2003/0060497 A1 | 3/2003 | Gerlach | ...... | 514/414 |
| 2003/0125371 A1 | 7/2003 | Elokdah et al. | ...... | 514/419 |
| 2004/0116504 A1 | 6/2004 | Elokdah et al. | ...... | 514/419 |
| 2004/0122070 A1 | 6/2004 | Jennings | ...... | 514/374 |
| 2004/0138283 A1 | 7/2004 | Jennings et al. | ...... | 514/414 |
| 2004/0204417 A1 | 10/2004 | Perez et al. | ...... | 514/249 |
| 2005/0070584 A1 | 3/2005 | Havran et al. | ...... | 514/357 |
| 2005/0070585 A1 | 3/2005 | Elokdah et al. | ...... | 514/364 |
| 2005/0070587 A1 | 3/2005 | Elokdah et al. | ...... | 514/381 |
| 2005/0070592 A1 | 3/2005 | Gundersen | ...... | 514/415 |
| 2005/0096377 A1 | 5/2005 | Hu | ...... | 514/419 |
| 2005/0113428 A1 | 5/2005 | Gopalsamy et al. | ...... | 514/364 |

(Continued)

FOREIGN PATENT DOCUMENTS

DE    3147276 A1    11/1981

(Continued)

OTHER PUBLICATIONS

Crandall, D. L. et al., "Characterization and comparative evaluation of a structurally unique PAI-1 inhibitor exhibiting oral in-vivo efficacy," *Journal of Thrombosis and Haemostasis*, Mar. 17, 2004, 2: 1422-1428.

(Continued)

*Primary Examiner*—Kamal A. Saeed
*Assistant Examiner*—Janet L. Coppins
(74) *Attorney, Agent, or Firm*—Mabel Ng

(57) ABSTRACT

The invention formula substituted 3-alkyl and 3-arylalkyl 1H indol-1yl acetic acid derivatives which are useful as inhibitors of plasminogen activator inhibitor (PAI-1) useful for treating fibrinolytic disorders, the compounds having the structure

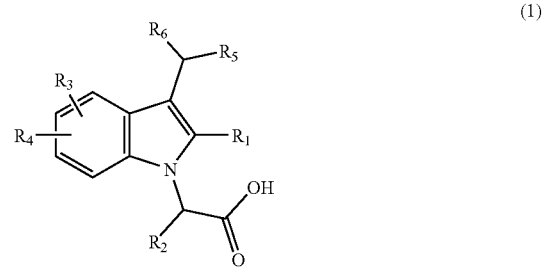

(1)

wherein:
$R_1, R_2, R_3, R_4, R_5, R_6$, and $R_7$ are as defined herein or a pharmaceutically acceptable salt or ester form thereof.

38 Claims, No Drawings

U.S. PATENT DOCUMENTS

| | | | |
|---|---|---|---|
| 2005/0113436 A1 | 5/2005 | Elokdah et al. | 514/411 |
| 2005/0113438 A1 | 5/2005 | Hu et al. | 514/414 |
| 2005/0113439 A1 | 5/2005 | Hu | 514/414 |
| 2005/0119296 A1 | 6/2005 | Elokdah et al. | 514/300 |
| 2005/0119326 A1 | 6/2005 | Havran et al. | 514/414 |
| 2005/0119327 A1 | 6/2005 | Hu | 514/414 |
| 2005/0215626 A1 | 9/2005 | Havran et al. | 514/469 |

FOREIGN PATENT DOCUMENTS

| | | |
|---|---|---|
| DE | 43 38 770 A1 | 5/1995 |
| DE | 19543639 A1 | 5/1997 |
| DE | 19753522 A1 | 6/1999 |
| EP | 0 416 609 A2 | 3/1991 |
| EP | 0 508 723 A1 | 10/1992 |
| EP | 0 512 570 A1 | 11/1992 |
| EP | 0 540 956 A1 | 5/1993 |
| EP | 0 655 439 A2 | 5/1995 |
| EP | 0 759 434 A1 | 2/1997 |
| EP | 0 819 686 A1 | 1/1998 |
| EP | 0 822 185 A1 | 2/1998 |
| EP | 0 955 299 A1 | 11/1999 |
| EP | 1 092 716 A2 | 4/2001 |
| EP | 1 156 045 A1 | 11/2001 |
| FR | 2 244 499 A1 | 4/1975 |
| FR | 2 777 886 A1 | 10/1999 |
| FR | 2 799 756 A1 | 4/2001 |
| GB | 1 321 433 | 6/1973 |
| WO | 94/13637 A1 | 6/1994 |
| WO | 94/14434 A1 | 7/1994 |
| WO | 94/26738 A1 | 11/1994 |
| WO | 95/10513 A1 | 4/1995 |
| WO | 96/06840 A1 | 3/1996 |
| WO | 96/21656 A1 | 7/1996 |
| WO | 96/26207 A1 | 8/1996 |
| WO | 96/32379 A1 | 10/1996 |
| WO | 97/09308 A1 | 3/1997 |
| WO | 97/43260 A1 | 11/1997 |
| WO | 97/48697 A1 | 12/1997 |
| WO | WO 97/48697 | 12/1997 |
| WO | 98/08818 A1 | 3/1998 |
| WO | 99/28297 A1 | 6/1999 |
| WO | 99/43651 A2 | 9/1999 |
| WO | 99/43672 A1 | 9/1999 |
| WO | 99/46260 A1 | 9/1999 |
| WO | WO 99/43654 | 9/1999 |
| WO | WO 99/50268 | 10/1999 |
| WO | 99/58519 A1 | 11/1999 |
| WO | 99/61435 A1 | 12/1999 |
| WO | 00/32180 A2 | 6/2000 |
| WO | 00/35919 A1 | 6/2000 |
| WO | WO 00/32180 | 6/2000 |
| WO | WO-00/32180 * | 6/2000 |
| WO | 00/46195 A1 | 8/2000 |
| WO | 00/46197 A1 | 8/2000 |
| WO | 00/64876 A1 | 11/2000 |
| WO | 00/64888 A1 | 11/2000 |
| WO | 01/12187 A2 | 2/2001 |
| WO | 02/30895 A2 | 4/2002 |
| WO | 02/072549 A1 | 9/2002 |
| WO | 03/000253 A1 | 1/2003 |
| WO | 03/031409 A1 | 4/2003 |
| WO | 03/068742 A1 | 8/2003 |
| WO | 03/087087 A2 | 10/2003 |
| WO | 2004/052854 A1 | 6/2004 |

OTHER PUBLICATIONS

Guzzo, P.R. et al., "Synthesis of a conformationally constrained threonin-valine dipeptide mimetic: design of a potential inhibitor of plasminogen activator inhibitor-1," Tetrahedron Letters, *Tetrahedron Letters*, 43(1), 41-43 (2002).

Charlton, Peter, "The status of plasminogen activator inhibitor-1 as a therapeutic target," Expert *Opinion On Investigational Drugs*, (May 1997), vol. 6, No. 5, pp. 539-554.

Malamas, M.S. et al. "Characterization and comparative evaluation of a structurally unique PAI-1 inhibitor exhibiting oral in-vivo efficacy," *Journal of Medicinal Chemistry*, 43(7):1293-1310.

Da Settimo, A. et al., "Reaction of indole derivatives with bromine, substitution, oxidation, and dimerization," *J Org Chem*, 1970, 35(8):2546-2551.

Chitra Kirshnamurti et al., Blood, Mar. 1987, 798-803, 69(3).

Christopher F. Reilly et al., Arteriosclerosis and Thrombosis, Sep./Oct. 1991, 1276-1286, 11(5).

Peter Carmeliet et al., J. Clin. Investigations, 1993, 2756-2760, 92.

E. Rocha et al., Fibrinolysis, 1994, 294-303, 8.

Justa Aznar et al., Haemostasis, 1994, 243-251, 24.

B.J. Biemond et al., Circulation, 1995, 1175-1181, 91(4).

Marcel Levi et al., Circulation, Jan. 1992, 305-312, 85(1).

Thomas K. Nordt et al., J. Clin. Endocrinology and Metabolism, 2000, 1563-1568, 85(4).

E. Daci et al., J. Bone and Mineral Research, 2000, 1510-1516, 15(8).

U.S. Appl. No. 10/947,710, filed Sep. 23, 2004, Commons et al.
U.S. Appl. No. 10/947,711, filed Sep. 23, 2004, Gopalsamy et al.
U.S. Appl. No. 11/208,777, filed Aug. 22, 2005, Commons et al.
U.S. Appl. No. 11/208,772, filed Aug. 22, 2005, Commons.
U.S. Appl. No. 11/208,775, filed Aug. 22, 2005, Commons et al.

Aggarwal et al., "A catalytic antibody programmed for torsional activation of amide bond hydrolysis," *Chem. Eur. J.*, Jan. 25, 2003, 9(13), 3132-3142.

Ballantine, J. A., "The Chemistry of bacteria," *Journal of the Chemical Society Abstracts*, 1957, 2222-2227.

Delgado et al., Journal of Organic Chemistry (1993), 58(10), pp. 2862-2866.

Dillard R. D. et al., "Indole Inhibitors of Human Nanopancreatic Secretory Phospholipase A2I. Indole-3-Acetamides", *Journal of Medicinal Chemistry, American Chemical Society*, 39(26), 5119-5136.

Hipskind, P. A. et al., "Potent and selective 1,2,3-trusubstituted indole NPY Y-1 antagonists," *J Med Chem*, 1997, 40(23), 3712-3714.

Julia et al., CA 57:49169, 1962.

Malamas, M. S. et al., "Antihyperglycemic activity of new 1,2,4-oxadiazolidine-3,5-diones," *Eur. J. Med. Chem.*, 2001, 36, 34-42.

Malamas, M.S. et al. "Novel benzofuran and benzothiophene biphenyls as inhibitors of protein tyrosin phosphatase 1B with antihyperglycemic properties," *Journal of Medicinal Chemistry*, Apr. 6, 2000, 43(7), 1293-1310.

Moody et al., CA 120:298300, 1994.

Shengeliya, M. S. et al., "N-Glycosides of 5-amino-2-(ethoxycarbonyl)indole," *Zhurnal Organicheskoi Khimii*, 1986, 22(9),1868-1873.

* cited by examiner

SUBSTITUTED 3-ALKYL AND 3-ARYLALKYL 1H-INDOL-1YL ACETIC ACID DERIVATIVES AS INHIBITORS OF PLASMINOGEN ACTIVATOR INHIBITOR-1 (PAI-1)

This application claims priority from co-pending provisional application Ser. No. 60/432,330 filed on Dec. 10, 2002, the entire disclosure of which is hereby incorporated by reference.

This invention relates to substituted 3-alkyl and 3-arylalkyl 1H-indol-1-yl acetic derivatives which are useful as inhibitors of plasminogen activator inhibitor-1 (PAI-1) and therapeutic compositions containing such compounds for treating conditions resulting from fibrinolytic disorders such as deep vein thrombosis and coronary heart disease, and pulmonary fibrosis.

BACKGROUND OF INVENTION

Plasminogen activator inhibitor-1 (PAI-1) is a major regulatory component of the plasminogen-plasmin system. PAI-1 is the principal physiologic inhibitor of both tissue type plasminogen activator (tPA) and urokinase type plasminogen activator (uPA). Elevated plasma levels of PAI-1 have been associated with thrombotic events as indicated by animal experiments (Krishnamurti, *Blood*, 69, 798 (1987); Reilly, *Arteriosclerosis and Thrombosis*, 11, 1276 (1991); Carmeliet, *Journal of Clinical Investigations*, 92, 2756 (1993)) and clinical studies (Rocha, *Fibrinolysis*, 8, 294, 1994; Aznar, *Haemostasis* 24, 243 (1994)). Antibody neutralization of PAI-1 activity resulted in promotion of endogenous thrombolysis and reperfusion (Biemond, *Circulation*, 91, 1175 (1995); Levi, *Circulation* 85, 305, (1992)). Elevated levels of PAI-1 have also been implicated in diseases of women such as polycystic ovary syndrome (Nordt, *Journal of Clinical Endocrinology and Metabolism*, 85, 4, 1563 (2000)) and bone loss induced by estrogen deficiency (Daci, *Journal of Bone and Mineral Research*, 15, 8, 1510 (2000)). Accordingly, agents that inhibit PAI-1 would be of utility in treating conditions originating from fibrinolytic disorder such as deep vein thrombosis, coronary heart disease, pulmonary fibrosis, polycystic ovary syndrome, etc.

WO 99/43654 and WO 99/43651 describe indole derivatives of formula I as inhibitors phospholipase enzymes useful in preventing inflammatory conditions.

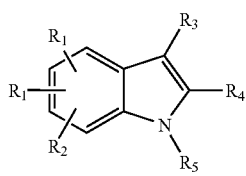

(I)

WO 99/50268 and WO 00/32180 disclose substituted indolealkanoic acids of formula (I) useful for the treatment of diabetic complications and reducing serum glucose and triglyceride levels.

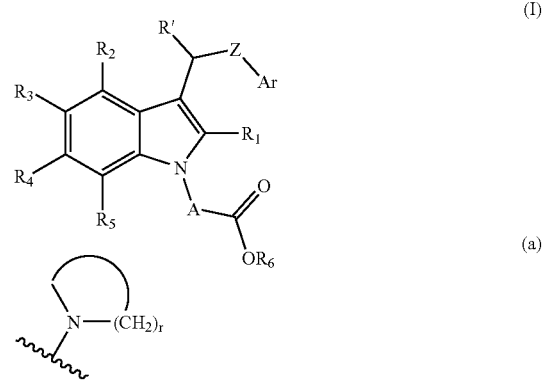

(I)

(a)

wherein: A is a $C_1$-$C_4$ alkylene group optionally substituted with $C_1$-$C_2$ alkyl or halogen, Z is a bond, O, S, C(O)NH, or $C_1$-$C_3$ alkylene optionally substituted with $C_1$-$C_2$-alkyl, $R_2$, $R_3$, $R_4$, and $R_5$ are independently hydrogen, halogen, nitro, $C_1$-$C_6$ alkyl, OR, Sr, S)O)R, S(O)$_2$R, C(O)NR$_2$, phenyl, heteroaryl, phenoxy, or a group of formula (a); $R_a$ is H, $C_1$-$C_6$ alkyl, fluoro, or trifluoromethyl; and Ar is aryl or heteroaryl.

EP 0655439 describes 5,6 fused ring bicyclic compounds including indoles, benzofurans, and benzothiophenes corresponding the general formula (I), below, as platelet aggregation inhibitors.

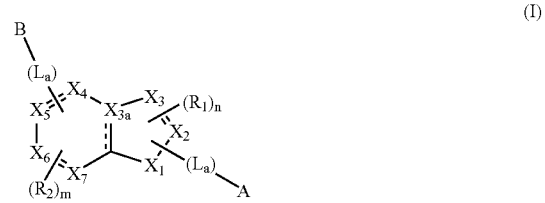

(I)

U.S. Pat. No. 5,612,360 describes tetrazolylphenyl-substituted heterocycles of formula (I) as angiotensin II inhibitors.

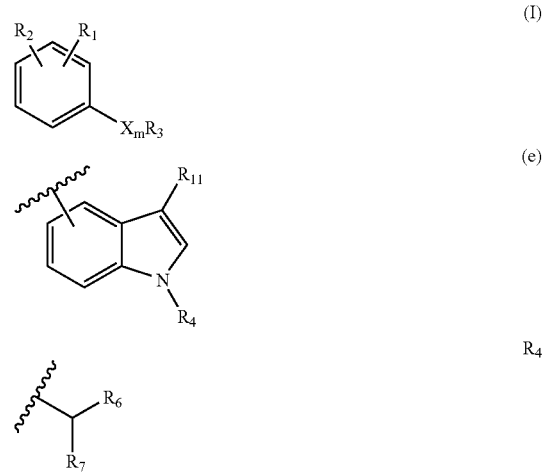

(I)

(e)

wherein: $R_1$ is —COOH, —S(O)$_3$H, —PO$_3$H$_2$, —C(O)NHSO$_2$R$_8$, or 5-tetrazolyl; $R_2$ is H —OH, —OAc, halogen, $C_1$-$C_4$ alkyl, or $C_1$-$C_4$ alkoxy; $R_3$ is substituted benzimidazole, indazole, or indole (e); $R_6$ is (CH$_2$)$_p$R$_1$, CONH(1-4C alkyl), CONH(1-4C trifluoroalkyl), $R_7$ is $C_4$-$C_9$ alkyl, $C_4$-$C_9$ trifluoroalkyl, $C_4$-$C_9$ alkenyl, or $C_4$-$C_9$ trifluoroalkeny; $R_{11}$ is hydrogen, $C_1$ to $C_4$ alkyl, halogen, or (CH$_2$)$_n$phenyl.

WO 9748697 describes substituted azabicyclic compounds including indoles, 2,3-dihydro-1H-indoles, and benzimidazoles of formula (I) for the treatment of conditions ameliorated by the administration of an inhibitor of tumor necrosis factor.

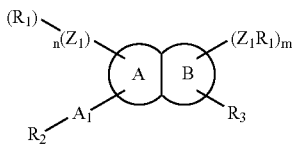

(I)

wherein: A is a five-membered aza heterocycle; B is a six membered aza heterocycle or an optionally substituted benzene ring; $Z_1$ is bond, O, S, NH; $A_1$ is bond, $C_1$-$C_6$ alkyl, $C_2$-$C_6$ alkenylene, or $C_2$-$C_6$ alkynylene; $R_1$ is hydrogen or optionally substituted $C_1$-$C_4$ alkyl, lower alkenyl or lower alkynyl; $R_2$ is hydrogen, alkenyl, alkyl, alkylsulfinyl, alkylsulphonyl, alkylthio, aryl, arylalkoxy, arylalkylsulphinyl, arylalkylsulphonyl, arylalkylthio, aryloxy, arylsulphinyl, arylsulphonyl, arylthio, —CN, cycloalkenyl, cycloalkenoxy, cycloalkyl, cycloalkyloxy, heteroaryl, heteroarylalkyloxy, heteroaryloxy, —OH, —SO$_2$NR$_4$R$_5$, —NR$_4$SO$_2$R$_5$, —NR$_4$R$_5$, —C(O)R$_5$, —C(O)C(O)R$_5$, —O(C=O)NR$_4$R$_5$, —C(O)OR$_5$, —O(C=O)NR$_4$R$_5$; $R_3$ is carboxamide, acyl, substituted alkenyl, substituted alkyl, acylamino, oximino, alkynyl, ketomethyl, aminoalkyl, sulfonylmethyl, sulfinylmethyl, CF$_2$OR, alkylamino, alkoxy, alkylsulfanyl, sulfinyl, acyloxy, sulfonyl, OCF$_2$R, azo, aminosulfonyl, sulfonylamino, or aminooxalyl.

SUMMARY OF THE INVENTION

This invention relates to compounds of formula (I):

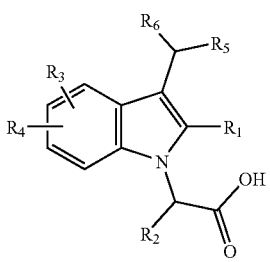

(I)

wherein:

$R_1$ is hydrogen, $C_1$-$C_6$ alkyl, $C_3$-$C_6$ cycloalkyl, —CH$_2$—C$_3$—C$_6$ cycloalkyl, or C perfluoroalkyl, preferably —CF$_3$, wherein the alkyl and cycloalkyl groups may be optionally substituted by halogen, —CN, $C_1$-$C_6$ alkoxy, —OH, —NH$_2$, or —NO$_2$;

$R_2$ is hydrogen, $C_1$-$C_8$ alkyl, $C_3$-$C_6$ cycloalkyl, —CH$_2$—C$_3$—C$_6$ cycloalkyl, thienyl, CH$_2$-thienyl, furanyl, CH$_2$-furanyl, oxazoyl, CH$_2$-oxazoyl, phenyl, benzyl, or CH$_2$-napthyl, wherein the alkyl group and the rings of the cycloalkyl, thienyl, furanyl, oxazoyl, phenyl, benzyl, and napthyl groups may be optionally substituted by from 1 to 3 groups selected from halogen, $C_1$-$C_3$ alkyl, $C_1$-$C_3$ perfluoroalkyl, preferably —CF$_3$, —O—C$_1$-$C_3$ perfluoroalkyl, preferably —OCF$_3$, —S—C$_1$-$C_3$ perfluoroalkyl, preferably —SCF$_3$, $C_1$-$C_3$ alkoxy, —OCHF$_2$, —CN, —COOH, —CH$_2$CO$_2$H, —C(O)CH$_3$, —C(O)OR$_7$, —C(O)NH$_2$—S(O)$_2$CH$_3$, —OH, —NH$_2$, or —NO$_2$;

$R_3$ is hydrogen, halogen, $C_1$-$C_6$ alkyl, $C_1$-$C_3$ perfluoroalkyl, preferably —CF$_3$, $C_1$-$C_6$ alkoxy, $C_3$-$C_6$ cycloalkyl, or —CH$_2$—C$_3$—C$_6$ cycloalkyl;

$R_4$ is $C_3$-$C_8$ alkyl, $C_3$-$C_6$ cycloalkyl, —CH$_2$—C$_3$—C$_6$ cycloalkyl, thienyl, CH$_2$-thienyl, furanyl, oxazoyl, phenyl, benzo[b]furan-2-yl, benzo[b]thien-2-yl, benzo[1,3]dioxol-5-yl, or naphthyl, wherein the alkyl group and the rings of the cycloalkyl, thienyl, furanyl, oxazoyl, phenyl, benzofuranyl, benzothienyl, and napthyl groups may be optionally substituted by from 1 to 3 groups selected from halogen, $C_1$-$C_3$ alkyl, $C_1$-$C_3$ perfluoroalkyl, preferably —CF$_3$, —O—C$_1$-$C_3$ perfluoroalkyl, preferably —OCF$_3$, —S—C$_1$-$C_3$ perfluoroalkyl, preferably —SCF$_3$, $C_1$-$C_3$ alkoxy, —OCHF$_2$, —C(O)CH$_3$, —C(O)OR$_7$, —C(O)NH$_2$, —S(O)$_2$CH$_3$, —OH, —NH$_2$, or —NO$_2$;

$R_5$ is $C_1$-$C_8$ alkyl, $C_3$-$C_6$ cycloalkyl, —CH$_2$—C$_3$-$C_6$ cycloalkyl, pyridinyl, —CH$_2$-pyridinyl, thienyl, CH$_2$-thienyl, furanyl, CH$_2$-furanyl, oxazoyl, CH$_2$-oxazoyl, phenyl, benzyl, benzo[b]furan-2-yl, benzo[b]thien-2-yl, benzo[1,3]dioxol-5-yl, naphthyl, CH$_2$-naphyl, 9H-fluoren-1-yl, 9H-fluoren4-yl, 9H-fluoren-9-yl, 9-fluorenone-1-yl, 9-fluorenone-2-yl, 9-fluorenone4-yl, or CH$_2$-9H-fluoren-9-yl, wherein the alkyl group and the rings of the cycloalkyl, pyridinyl, thienyl, furanyl, oxazoyl, phenyl, benzyl, benzofuranyl, benzothienyl, napthyl, fluorenyl, and fluorenone groups may be optionally substituted by from 1 to 3 groups selected from halogen, $C_1$-$C_3$ alkyl, $C_3$-$C_6$ cycloalkyl, $C_1$-$C_3$ perfluoroalkyl, preferably —CF$_3$, —O—C$_1$-$C_3$ perfluoroalkyl, preferably —OCF$_3$, —S—C$_1$-$C_3$ perfluoroalkyl, preferably —SCF$_3$, $C_1$-$C_3$ alkoxy, phenoxy, —OCHF$_2$, —CN, —COOH, —CH$_2$CO$_2$H, —C(O)CH$_3$, —C(O)OR$_7$, —C(O)NH$_2$, —S(O)$_2$CH$_3$, —OH, —NH$_2$, or —NO$_2$, wherein the phenoxy group may be optionally substituted by from 1 to 3 groups selected from halogen, $C_1$-$C_3$ alkyl, or $C_1$-$C_3$ perfluoroalkyl, preferably —CF$_3$;

$R_6$ is hydrogen, $C_1$-$C_8$ alkyl, $C_3$-$C_6$ cycloalkyl, —CH$_2$—C$_3$-$C_6$ cycloalkyl, pyridyl thienyl, CH$_2$-thienyl, furanyl, CH$_2$-furanyl, oxazoyl, CH$_2$-oxazoyl, phenyl, benzyl, benzo[b]furan-2-yl, benzo[b]thien-2-yl, benzo[1,3]dioxol-5-yl, CH$_2$-1-naphthyl, or CH$_2$-2-naphyl, wherein the alkyl group and the rings of the cycloalkyl, thienyl, furanyl, oxazoyl, phenyl, benzyl, benzofuranyl, benzothienyl, and napthyl groups may be optionally substituted by from 1 to 3 groups selected from halogen, $C_1$-$C_3$ alkyl, $C_1$-$C_3$ perfluoroalkyl, preferably —CF$_3$, —O—C$_1$-$C_3$ perfluoroalkyl, preferably —OCF$_3$, —S—C$_1$-$C_3$ perfluoroalkyl, preferably —SCF$_3$, $C_1$-$C_3$ alkoxy, —OCHF$_2$, —CN, —COOH, —CH$_2$CO$_2$H, —C(O)CH$_3$, —C(O)OR$_7$, —C(O)NH$_2$, —S(O)$_2$CH$_3$, —OH, —NH$_2$, or —NO$_2$;

or $R_5$ and $R_6$ taken together may be $C_3$-$C_6$ cycloalkyl, 3-indan-1-yl, 1,2,3,4-tetrahydronaphthalen-1-yl, chroman-4-yl, 4H-chromen-4-yl, thiochroman-4-yl, 9H-fluoren-9-yl, 9,10-dihydroanthracen-9-yl, 9H-xanthen-9-yl, 9H-thioxanthen-9-yl, 6,7,8,9-tetrahydro-5H-benzocyclohepten-5-yl, or 10,11-dihydro-5H-dibenzo[a,d]cyclohepten-5-yl, wherein these groups may be optionally substituted by from 1 to 3 groups selected from halogen, $C_1$-$C_3$ alkyl, $C_1$-$C_3$ perfluoroalkyl, preferably —CF₃, —O—C₁-C₃ perfluoroalkyl, preferably —OCF₃, —S—C₁-C₃ perfluoroalkyl preferably —SCF₃, C₁-C₃ alkoxy, —OCHF₂, —CN, —COOH, —CH₂CO₂H, —C(O)CH₃, —C(O)OR₇, —C(O)NH₂, —S(O)₂CH₃, —OH, —NH₂, or —NO₂; and R₇ is C₁-C₆ alkyl, C₃-C₆ cycloalkyl, —CH₂—C₃-C₆ cycloalkyl, or benzyl;

or a pharmaceutically acceptable salt or ester form thereof.

DETAILED DESCRIPTION OF THE INVENTION

Preferred compounds of this invention are those of the formula (I) wherein R₁-R₃ and R₅-R₇ are as defined above, and R₄ is thienyl, furanyl, oxazoyl, phenyl, benzo[b]furan-2-yl, benzo[b]thien-2-yl, benzo[1,3]dioxol-5-yl, or naphthyl, wherein the rings of the thienyl, furanyl, oxazoyl, phenyl, benzofuranyl, benzothienyl, and napthyl groups may be optionally substituted by from 1 to 3 groups selected from halogen, C₁-C₃ alkyl, C₁-C₃ perfluoroalkyl, preferably —CF₃, —O—C₁-C₃ perfluoroalkyl, preferably —OCF₃, —S—C₁-C₃ perfluoroalkyl preferably —SCF₃, C₁-C₃ alkoxy, —OCHF₂, —CN, —COOH, —CH₂CO₂H, —C(O)CH₃, —CO₂R₈, —C(O)NH₂, —S(O)₂CH₃, —OH, —NH₂, or —NO₂;

or a pharmaceutically acceptable salt or ester form thereof.

More preferred compounds of this invention include those of formula II:

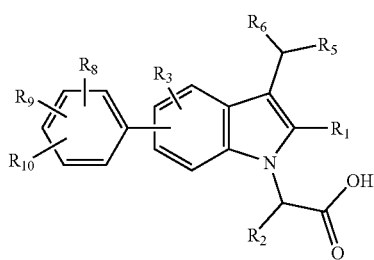

(II)

wherein:

R₁ is hydrogen, C₁-C₆ alkyl, C₃-C₆ cycloalkyl, —CH₂—C₃-C₆ cycloalkyl, or C₁-C₃ perfluoroalkyl, preferably —CF₃, wherein the alkyl and cycloalkyl groups may be optionally substituted by halogen, —CN, C₁-C₆ alkoxy, —OH, —NH₂, or —NO₂;

R₂ is hydrogen, C₁-C₈ alkyl, C₃-C₆ cycloalkyl, or —CH₂—C₃-C₆ cycloalkyl, wherein the alkyl group and the rings of the cycloalkyl groups may be optionally substituted by from 1 to 3 groups selected from halogen, C₁-C₃ alkyl, C₁-C₃ perfluoroalkyl, preferably —CF₃, —O—C₁-C₃ perfluoroalkyl, preferably —OCF₃, —S—C₁-C₃ perfluoroalkyl, preferably —SCF₃, C₁-C₃ alkoxy, —OCHF₂, —CN, —COOH, —CH₂CO₂H, —C(O)CH₃, —C(O)OR₇, —C(O)NH₂, —S(O)₂CH₃, —OH, —NH₂, or —NO₂;

R₃ is hydrogen, halogen, C₁-C₆ alkyl, C₁-C₃ perfluoroalkyl, preferably —CF₃, C₁-C₆ alkoxy, C₃-C₆ cycloalkyl, or —CH₂—C₃-C₆ cycloalkyl;

R₅ is C₁-C₈ alkyl, C₃-C₆ cycloalkyl, —CH₂—C₃-C₆ cycloalkyl, phenyl, benzyl, thienyl, naphthyl, or CH₂-naphyl, wherein the alkyl group and the rings of the cycloalkyl, phenyl, thienyl and benzyl groups may be optionally substituted by from 1 to 3 groups selected from halogen, C₁-C₃ alkyl, C₃-C₆ cycloalkyl, C₁-C₃ perfluoroalkyl, preferably —CF₃, —O—C₁-C₃ perfluoroalkyl, preferably —OCF₃, —S—C₁-C₃ perfluoroalkyl, preferably —SCF₃, C₁-C₃ alkoxy, —OCHF₂, —CN, —COOH, —CH₂CO₂H, —C(O) CH₃, —C(O)NH₂, —S(O)₂CH₃, —OH, —NH₂, —NO₂, or phenoxy; wherein the phenoxy group may be optionally substituted by from 1 to 3 groups selected from halogen, C₁-C₃ alkyl, or C₁-C₃ perfluoroalkyl, preferably —CF₃;

R₆ is hydrogen, C₁-C₈ alkyl, C₃-C₆ cycloalkyl, or —CH₂—C₃-C₆ cycloalkyl, wherein the alkyl group and the rings of the cycloalkyl groups may be optionally substituted by from 1 to 3 groups selected from halogen, C₁-C₃ alkyl, C₁-C₃ perfluoroalkyl, preferably —CF₃, —O—C₁-C₃ perfluoroalkyl, preferably —OCF₃, —S—C₁-C₃ perfluoroalkyl, preferably —SCF₃, C₁-C₃ alkoxy, —OCHF₂, —CN, —COOH, —CH₂CO₂H, —C(O)CH₃, —C(O)OR₇, —C(O)NH₂, —S(O)₂CH₃, —OH, —NH₂, or —NO₂;

or R₅ and R₆ taken together may be a C₃-C₆ cycloalkyl group optionally substituted by from 1 to 3 groups selected from halogen, C₁-C₃ alkyl, C₁-C₃ perfluoroalkyl, preferably —CF₃, —O—C₁-C₃ perfluoroalkyl, preferably —OCF₃, —S—C₁-C₃ perfluoroalkyl, preferably —SCF₃, C₁-C₃ alkoxy, —OCHF₂, —CN, —COOH, —CH₂CO₂H, —C(O) CH₃, —C(O)NH₂, —S(O)₂CH₃, —OH, —NH₂, or —NO₂;

R₈, R₉, R₁₀ are each independently hydrogen, halogen, C₁-C₃ alkyl, C₁-C₃ perfluoroalkyl, preferably —CF₃, —O—C₁-C₃ perfluoroalkyl, preferably —OCF₃, —S—C₁-C₃ perfluoroalkyl, preferably —SCF₃, C₁-C₃ alkoxy, —OCHF₂, —C(O)CH₃, —C(O)NH₂, —S(O)—₂CH₃, —OH, —NH₂, or —NO₂;

or a pharmaceutically acceptable salt or ester form thereof.

Even more preferred compounds of this invention include those of formula III:

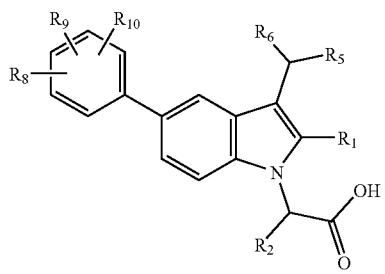

(III)

wherein:

R₁ is hydrogen or C₁-C₆ alkyl;

R₂ is hydrogen or C₁-C₃ alkyl, optionally substituted by halogen;

R₅ is C₁-C₈ alkyl, C₃-C₆ cycloalkyl, —CH₂—C₃-C₆ cycloalkyl, phenyl, benzyl, or thienyl wherein the alkyl group and the rings of the cycloalkyl, phenyl, thienyl and benzyl groups may be optionally substituted by from 1 to 3 groups selected from halogen, C₁-C₃ alkyl, C₃-C₆ cycloalkyl, C₁-C₃ perfluoroalkyl, preferably —CF₃, —O—C₁-C₃ perfluoroalkyl, preferably —OCF₃, —S—C₁-C₃ perfluoroalkyl, preferably —SCF₃, C₁-C₃ alkoxy, —OCHF₂, —CN, —COOH, —CH₂CO₂H, —C(O)CH₃, —C(O)NH₂, —S(O)₂CH₃, —OH, —NH₂, or —NO₂;

$R_6$ is hydrogen or $C_1$-$C_6$ alkyl, optionally substituted by halogen;

$R_8$, $R_9$, $R_{10}$ are each independently halogen, $C_1$-$C_3$ alkyl, $C_1$-$C_3$ perfluoroalkyl, preferably —$CF_3$, —O—$C_1$-$C_3$ perfluoroalkyl, preferably —$OCF_3$, —S—$C_1$-$C_3$ perfluoroalkyl preferably —$SCF_3$, $C_1$-$C_3$ alkoxy, —$OCHF_2$, —$C(O)CH_3$, —$C(O)NH_2$, —$S(O)_2CH_3$, —OH, —$NH_2$, or —$NO_2$;

or a pharmaceutically acceptable salt or ester form thereof.

The present invention is further directed to a method of inhibiting plasminogen activator inhibitor (PAI-1) in a mammal, the method comprising administering to a mammal in need thereof a therapeutically effective amount of a compound of formula I:

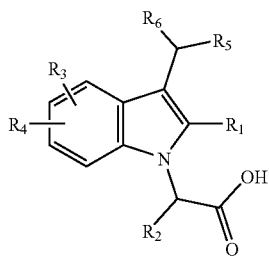

wherein:

$R_1$ is hydrogen, $C_1$-$C_6$ alkyl, $C_3$-$C_6$ cycloalkyl, —$CH_2$—$C_3$-$C_6$ cycloalkyl, or $C_1$-$C_3$ perfluoroalkyl, preferably —$CF_3$, wherein the alkyl and cycloalkyl groups may be optionally substituted by halogen, —CN, $C_1$-$C_6$ alkoxy, —OH, —$NH_2$, or —$NO_2$;

$R_2$ is hydrogen, $C_1$-$C_8$ alkyl, $C_3$-$C_6$ cycloalkyl, —$CH_2$—$C_3$-$C_6$ cycloalkyl, thienyl $CH_2$-thienyl, furanyl, $CH_2$-furanyl, oxazoyl, $CH_2$-oxazoyl, phenyl, benzyl, or $CH_2$-naphthyl, wherein the alkyl group and the rings of the cycloalkyl, thienyl, furanyl, oxazoyl, phenyl, benzyl, and naphthyl groups may be optionally substituted by from 1 to 3 groups selected from halogen, $C_1$-$C_3$ alkyl, $C_1$-$C_3$ perfluoroalkyl, preferably —$CF_3$, —O—$C_1$-$C_3$ perfluoroalkyl, preferably —$OCF_3$, —S—$C_1$-$C_3$ perfluoroalkyl, preferably —$SCF_3$, $C_1$-$C_3$ alkoxy, —$OCHF_2$, —CN, —COOH, —$CH_2CO_2H$, —$C(O)CH_3$, —$C(O)OR_7$, —$C(O)NH_2$, —$S(O)_2CH_3$, —OH, —$NH_2$, or —$NO_2$;

$R_3$ is hydrogen, halogen, $C_1$-$C_6$ alkyl, $C_1$-$C_3$ perfluoroalkyl, preferably —$CF_3$, $C_1$-$C_6$ alkoxy, $C_3$-$C_6$ cycloalkyl, or —$CH_2$—$C_3$-$C_6$ cycloalkyl;

$R_4$ is $C_3$-$C_8$ alkyl, $C_3$-$C_6$ cycloalkyl, —$CH_2$—$C_3$-$C_6$ cycloalkyl, thienyl, $CH_2$-thienyl, furanyl, oxazoyl, phenyl, benzo[b]furan-2-yl, benzo[b]thien-2-yl, benzo[1,3]dioxol-5-yl, or naphthyl, wherein the alkyl group and the rings of the cycloalkyl, thienyl, furanyl, oxazoyl, phenyl, benzofuranyl, benzothienyl, and naphthyl groups may be optionally substituted by from 1 to 3 groups selected from halogen, $C_1$-$C_3$ alkyl, $C_1$-$C_3$ perfluoroalkyl, preferably —$CF_3$, —O—$C_1$-$C_3$ perfluoroalkyl, preferably —$OCF_3$, —S—$C_1$-$C_3$ perfluoroalkyl, preferably —$SCF_3$, $C_1$-$C_3$ alkoxy, —$OCHF_2$, —$C(O)CH_3$, —$C(O)OR_7$, —$C(O)NH_2$, —$S(O)_2CH_3$, —OH, —$NH_2$, or —$NO_2$;

$R_5$ is $C_1$-$C_8$ alkyl, $C_3$-$C_6$ cycloalkyl, —$CH_2$—$C_3$-$C_6$ cycloalkyl, pyridinyl, —$CH_2$-pyridinyl, thienyl, $CH_2$-thienyl, furanyl, $CH_2$-furanyl, oxazoyl, $CH_2$-oxazoyl, phenyl, benzyl, benzo[b]furan-2-yl, benzo[b]thien-2-yl, benzo[1,3]dioxol-5-yl, naphthyl, $CH_2$-naphyl, 9H-fluoren-1-yl, 9H-fluoren-4-yl, 9H-fluoren-9-yl, 9-fluorenone-1-yl, 9-fluorenone-2-yl, 9-fluorenone-4-yl, or $CH_2$-9H-fluoren-9-yl, wherein the alkyl group and the rings of the cycloalkyl, pyridinyl, thienyl, furanyl, oxazoyl, phenyl, benzyl, benzofuranyl, benzothienyl, naphthyl, fluorenyl, and fluorenone groups may be optionally substituted by from 1 to 3 groups selected from halogen, $C_1$-$C_3$ alkyl, $C_3$-$C_6$ cycloalkyl, $C_1$-$C_3$ perfluoroalkyl, preferably —$CF_3$, —O—$C_1$-$C_3$ perfluoroalkyl, preferably —$OCF_3$, —S—$C_1$-$C_3$ perfluoroalkyl, preferably —$SCF_3$, $C_1$-$C_3$ alkoxy, phenoxy, —$OCHF_2$, —CN, —COOH, —$CH_2CO_2H$, —$C(O)CH_3$, —$C(O)OR_7$, —$C(O)NH_2$, —$S(O)_2CH_3$, —OH, —$NH_2$, or —$NO_2$, wherein the phenoxy group may be optionally substituted by from 1 to 3 groups selected from halogen, $C_1$-$C_3$ alkyl, or $C_1$-$C_3$ perfluoroalkyl, preferably —$CF_3$;

$R_6$ is hydrogen, $C_1$-$C_8$ alkyl, $C_3$-$C_6$ cycloalkyl, —$CH_2$—$C_3$-$C_6$ cycloalkyl, pyridyl thienyl, $CH_2$-thienyl, furanyl, $CH_2$-furanyl, oxazoyl, $CH_2$-oxazoyl, phenyl, benzyl, benzo[b]furan-2-yl, benzo[b]thien-2-yl, benzo[1,3]dioxol-5-yl, $CH_2$-1-naphthyl, or $CH_2$-2-naphyl, wherein the alkyl group and the rings of the cycloalkyl, thienyl, furanyl, oxazoyl, phenyl, benzyl, benzofuranyl, benzothienyl, and naphthyl groups may be optionally substituted by from 1 to 3 groups selected from halogen, $C_1$-$C_3$ alkyl, $C_1$-$C_3$ perfluoroalkyl, preferably —$CF_3$, —O—$C_1$-$C_3$ perfluoroalkyl, preferably —$OCF_3$, —S—$C_1$-$C_3$ perfluoroalkyl, preferably —$SCF_3$, $C_1$-$C_3$ alkoxy, —$OCHF_2$, —CN, —COOH, —$CH_2CO_2H$, —$C(O)CH_3$, —$C(O)OR_7$, —$C(O)NH_2$, —$S(O)_2CH_3$, —OH, —$NH_2$, or —$NO_2$;

or $R_5$ and $R_6$ taken together may be $C_3$-$C_6$ cycloalkyl, 3-indan-1-yl, 1,2,3,4-tetrahydronaphthalen-1-yl, chroman-4-yl, 4H-chromen-4-yl, thiochroman-4-yl, 9H-fluoren-9-yl, 9,10-dihydroanthracen-9-yl, 9H-xanthen-9-yl, 9H-thioxanthen-9-yl, 6,7,8,9-tetrahydro-5H-benzocyclohepten-5-yl, or 10,11-dihydro-5H-dibenzo[a,d]cyclohepten-5-yl, wherein these groups may be optionally substituted by from 1 to 3 groups selected from halogen, $C_1$-$C_3$ alkyl, $C_1$-$C_3$ perfluoroalkyl, preferably —$CF_3$, —O—$C_1$-$C_3$ perfluoroalkyl, preferably —$OCF_3$, —S—$C_1$-$C_3$ perfluoroalkyl, preferably —$SCF_3$, $C_1$-$C_3$ alkoxy, —$OCHF_2$, —CN, —COOH, —$CH_2CO_2H$, —$C(O)CH_3$, —$C(O)OR_7$, —$C(O)NH_2$, —$S(O)_2CH_3$, —OH, —$NH_2$, or —$NO_2$; and $R_7$ is $C_1$-$C_6$ alkyl, $C_3$-$C_6$ cycloalkyl, —$CH_2$—$C_3$-$C_6$ cycloalkyl, or benzyl;

or a pharmaceutically acceptable salt or ester form thereof.

Specific examples of compounds of the present invention include:

{5-(3-trifluoromethoxyphenyl)-3-[1-(4-trifluromethylphenyl)-ethyl]indol-1-yl}-acetic acid;

{3-[3,5-bistrifluoromethyl)benzyl]-5-[4-(trifluromethoxy)phenyl]-1H-indol-1-yl}acetic acid;

[3-3,5-bis(trifluoromethyl)benzyl)-5-(2,4-dichlorophenyl)-1H-indol-1yl]acetic acid;

{3-[3,5-bis(trifluoromethyl)benzyl]-5-[3(trifluoromethyl)phenyl]-1H-indol-1-yl}acetic acid;

{5-(3-chlorophenyl)-3-[1-(2-thienyl)ethyl]-1H-indol-1-yl}acetic acid;

[3-(1-phenylethyl)-5-(3-trifluoromethyl-phenyl)-indol-1-yl]acetic acid;

[3-(1-thiophen-2-yl-ethyl)-5-(3-trifluoromethylphenyl)-indol-1-yl]acetic acid;

[3-(1-cyclohexyl-ethyl)-5-(3-trifluoromethylphenyl)-indol-1-yl]acetic acid;

[3-(4-isopropyl-benzyl)-5-(3-trifluoromethyl phenyl)-indol-1-yl]acetic acid;

{5-(2,4-dichlorophenyl)-3-(1,3-dimethyl-butyl)-indol-1-yl] acetic acid;

[5-(2,4-dichloro-phenyl)-3-(1-phenyl ethyl)-indol-1-yl]acetic acid; and

[3-(1-cyclohexyl-ethyl))-5-(2,4-dichlorophenyl)-indol-1-yl] acetic acid, or a pharmaceutically acceptable salt or ester form thereof.

It will be understood that the substitution of the alkyl groups at $R_2$ and $R_6$ may include any degree of substitution of halogen possible for the alkyl chain in question. For instance, fluorination or perfluorination of an alkyl group could include —$CF_3$, —$CH_2CF_3$, —$CF_2$—$CF_3$, etc.

The preferred salt forms of the compounds herein include but are not limited to sodium salts, and potassium salts. Other useful salt forms of these compounds include those formed with pharmaceutically acceptable inorganic and organic bases known in the art. Salt forms prepared using inorganic bases include hydroxides, carbonates or bicarbonates of the therapeutically acceptable alkali metals or alkaline earth methals, such as sodium potassium, magnesium, calcium and the like. Acceptable organic bases include amines, such as benzylzmine, mono-, di- and trialkylamines, preferably those having alkyl groups of from 1 to 6 carbon atoms, more preferably 1 to 3 carbon atoms, such as methylamine, dimethylamine, trimethylamine, ethylamine, diethylamine, triethylamine, mono-, di-, and triethanolamine. Also useful are alkylene diamines containing up to 6 carbon atoms, such as hexamethylenediamine; cyclic saturated or unsaturated bases containing up to 6 carbon atoms, including pyrrolidine, peperidine, morpholine, piperazine and their N-alkyl and N-hydroxyalkyl derivatives, such as N-methyl-morpholine and N-(2-hyroxyethyl)-piperidine, or pyridine. Quaternary salts may also be formed, such as tetralkyl forms, such as tetramethyl forms, alkyl-alkanol forms, such as methyl-triethanol or trimethyl-monoethanol forms, and cyclic ammonium salt forms, such as N-methylpyridinium, N-methyl-N-(2-hydroxyethyl)-morpholinium, N,N-di-methylmorpholinium, N-mehtyl-N-(2-hydroxyethyl)-morpholinium, or N,N-dimethyl-piperidinium salt forms. These salt forms may be prepared using the acidic compound(s) of Formula I and procedures known in the art.

Ester forms of the compounds of this invention include straight chain alkyl esters having from 1 to 6 carbon atoms or branched chain alkyl groups containing 3 or 6 carbon atoms, including methyl, ethyl, propyl, butyl, 2-methylpropyl and 1,1-dimethylethyl esters. Other esters useful with this invention include those of the formula —$COOR_{11}$ wherein $R_{11}$ is selected from the formulae:

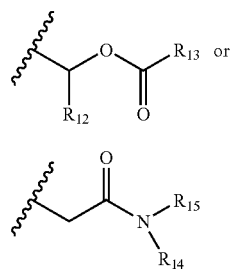

wherein $R_{12}$, $R_{13}$, $R_{14}$, $R_{15}$ are independently selected from hydrogen, alkyl of from 1 to 10 carbon atoms, aryl of 6 to 12 carbon atoms, arylalkyl of from 6 to 12 carbon atoms; heteroaryl or alkylheteroaryl wherein the heteroaryl ring is bound by an alkyl chain of from 1 to 6 carbon atoms.

Among the preferred ester forms of the compounds herein include but not limited to $C_1$-$C_6$ alkyl esters, $C_3$-$C_6$ branched alkyl esters, benzyl esters, etc.

As used herein, "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryl groups include phenyl, naphthyl and the like. As used herein, "heteroaryl" refers to a monocyclic or bicyclic aromatic group of from 1 to carbon atoms and 1 to 4 heteroatoms selected from oxygen, nitrogen and sulfur within at least one ring (if there is more than one ring). Such heteroaryl groups can have a single ring, such as pyridyl, pyrrolyl or furyl groups, or multiple condensed rings, such as indolyl, indolizinyl, benzofuranyl or benzothienyl groups. Preferred heteroaryls include pyridyl, pyrrolyl and furyl.

Unless otherwise limited by the definition for the aryl or heteroaryl groups herein, such groups can optionally be substituted with from 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, substituted alkyl, substituted alkoxy, substituted alkenyl, substituted alkynyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. Substituents on the alkyl, alkenyl, alkynyl, thioalkoxy and alkoxy groups mentioned above include halogens, CN, OH, and amino groups. Preferred substituents on the aryl groups herein include alkyl, alkoxy, halo, cyano, nitro, trihalomethyl, and thioalkoxy.

The compounds of the present invention are inhibitors of the serine protease inhibitor PAI-1, and are therefore useful in the treatment, inhibition, prevention or prophylaxis in a mammal, preferably in a human, of those processes which involve the production and/or action of PAI-1. Thus, the compounds of the invention are useful in the treatment or prevention of noninsulin dependent diabetes mellitus and cardiovascular disease caused by such condition, and prevention of thrombotic events associated with coronary artery and cerebrovascular disease. These compounds are also useful for inhibiting the disease process involving the thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery (such as joint replacement), and peripheral arterial occlusion. These compounds are also useful in treating stroke associated with or resulting from atrial fibrillation.

The compounds of the invention may also be used in the treatment of diseases associated with extracellular matrix accumulation, including, but not limited to, renal fibrosis, chronic obstructive pulmonary disease, polycystic ovary syndrome, restenosis, renovascular disease and organ transplant rejection.

The compounds of the invention may also be used in the treatment of malignancies, and diseases associated with neoangiogenesis (such as diabetic retinopathy).

The compounds in the invention may also be used in conjunction with and following processes or procedures involving maintaining blood vessel patency, including vascular surgery, vascular graft and stent patency, organ, tissue and cell implantation and transplantation.

The compounds in the invention may also be useful in the treatment of inflammatory diseases, septic shock and the vascular damage associated with infections.

The compounds of the invention are useful for the treatment of blood and blood products used in dialysis, blood storage in the fluid phase, especially ex vivo platelet aggregation. The present compounds may also be added to human plasma during the analysis of blood chemistry in hospital settings to determine the fibrinolytic capacity thereof.

The compounds in the present invention may also be used in combination with prothrombolytic, fibrinolytic and anticoagulant agents.

The compounds of the present invention may also be used to treat cancer including, but not limited to, breast and ovarian cancer, and as imaging agents for the identification of metastatic cancers.

The compounds of the invention may also be used in the treatment of Alzheimer's disease. This method may also be characterized as the inhibition of plasminogen activator by PAI-1 in a mammal, particularly a human, experiencing or subject to Alzhemier's disease. This method may also be characterized as a method of increasing or normalizing levels of plasmin concentration in a mammal, particularly those experiencing or subject to Alzheimer's disease.

The compounds of the invention may be used for the treatment of myelofibrosis with myeloid metaplasia by regulating stromal cell hyperplasia and increases in extracellular matrix proteins.

The compounds of the invention may also be used in conjunction with protease inhibitor—containing highly active antiretroviral therapy (HAART) for the treatment of diseases which originate from fibrinolytic impairment and hyper-coagulability of HIV-1 infected patients receiving such therapy.

The compounds of the invention may be used for the treatment of diabetic nephropathy and renal dialysis associated with nephropathy.

The compounds of the invention may be used to treat cancer, septicemia, obesity, insulin resistance, proliferative diseases such as psoriasis, improving coagulation homeostasis, cerebrovascular diseases, microvascular disease, hypertension, dementia, osteoporosis, arthritis, asthma, heart failure, arrhythmia, angina, and as a hormone replacement agent, treating, preventing or reversing progression of atherosclerosis, Alzheimer's disease, osteoporosis, osteopenia; reducing inflammatory markers, reducing C-reactive protein, or preventing or treating low grade vascular inflammation, stroke, dementia, coronary heart disease, primary and secondary prevention of myocardial infarction, stable and unstable angina, primary prevention of coronary events, secondary prevention of cardiovascular events, peripheral vascular disease, peripheral arterial disease, acute vascular syndromes, reducing the risk of undergoing a myocardial revascularization procedure, microvascular diseases such as nephropathy, neuropathy, retinopathy and nephrotic syndrome, hypertension, Type 1 and 2 diabetes and related diseases, hyperglycemia, hyperinsulinemia, malignant lesions, premalignant lesions, gastrointestinal malignancies, liposarcomas and epithelial tumors, proliferative diseases such as psoriasis, improving coagulation homeostasis, and/ or improving endothelial function, and all forms of cerebrovascular diseases.

The compounds of the invention may be used for the topical applications in wound healing for prevention of scarring.

Methods for the treatment, inhibition, prevention or prophylaxis in a mammal of each of the conditions or maladies listed herein are part of the present invention. Each method comprises administering to a mammal in need thereof a pharmaceutically or therapeutically effective amount of a compound of this invention, or a pharmaceutically acceptable salt or ester form thereof.

This invention also provides pharmaceutical compositions comprising a pharmaceutically or therapeutically effective amount of a compound of this invention, or a pharmaceutically acceptable salt or ester form thereof, either alone or in combination with one or more pharmaceutically acceptable carriers or excipients (i.e. pharmaceutically acceptable materials with no pharmacological effects). It will be understood that a pharmaceutically or therapeutically effective amount of a compound herein refers to an amount of the compound in question which will sufficiently inhibit the serine protease inhibitor PAI-1 in the mammal in need thereof to a sufficient extent to provide a desirable improvement in the condition in question or provide sufficient inhibition of the serine protease inhibitor PAI-1 to prevent, inhibit or limit the onset of the physiological basis for the malady or condition in question.

PROCESS OF THE INVENTION

The compounds of the present invention can be readily prepared according to the following reaction schemes or modification thereof using readily available starting materials, reagents and conventional synthetic procedures. It is also possible to make use of variants of these process steps, which in themselves are known to and well within the preparatory skill of the medicinal chemist. In the following reaction schemes, $R_1$-$R_{10}$ are selected from the groups defined above.

Method A

In Method A, indole, substituted on the benzene ring with bromide, iodine, or triflate, is cross-coupled with an aryl boronic acid in the presence of a palladium catalyst, such as Pd(PPh$_3$)$_4$, a base, such as Na$_2$CO$_3$ or NaHCO$_3$, in a solvent, such as water, dioxane, THF, toluene, methanol or ethanol, or in a mixed co-solvent system comprising two or more of the aforesaid solvents, at 50-110° C. Boronic acid derivatives of benzene, furan, thiophene, benz[b]thiophene and napthylene are described in the literature and many are presently commercially available. The aryl indole intermediates can be alkylated on nitrogen with esters of bromoacetic acid, preferably t-butyl bromoacetate, in the presence of a base, such as NaH, Na(SiMe$_3$)$_2$, or KOt-Bu, in DMF or THF, to afford aryl indo-1-yl acetic acid methyl or t-butyl esters. The aryl indo-1-yl acetic acid t-butyl esters can be condensed with either aldehydes or ketones in the presence of acid, such as acetic or trifluoroacetic acid, and a reducing reagent, such as triethylsilane, in an inert solvent at 0-60° C. Any inert solvent, such as DCM, DCE, or toluene, can be used. Reduction of the benzylidine intermediate and cleavage of the t-butyl ester happens concomitantly. The indol-1-yl acetic acid products can be purified by chromatography or by HPLC.

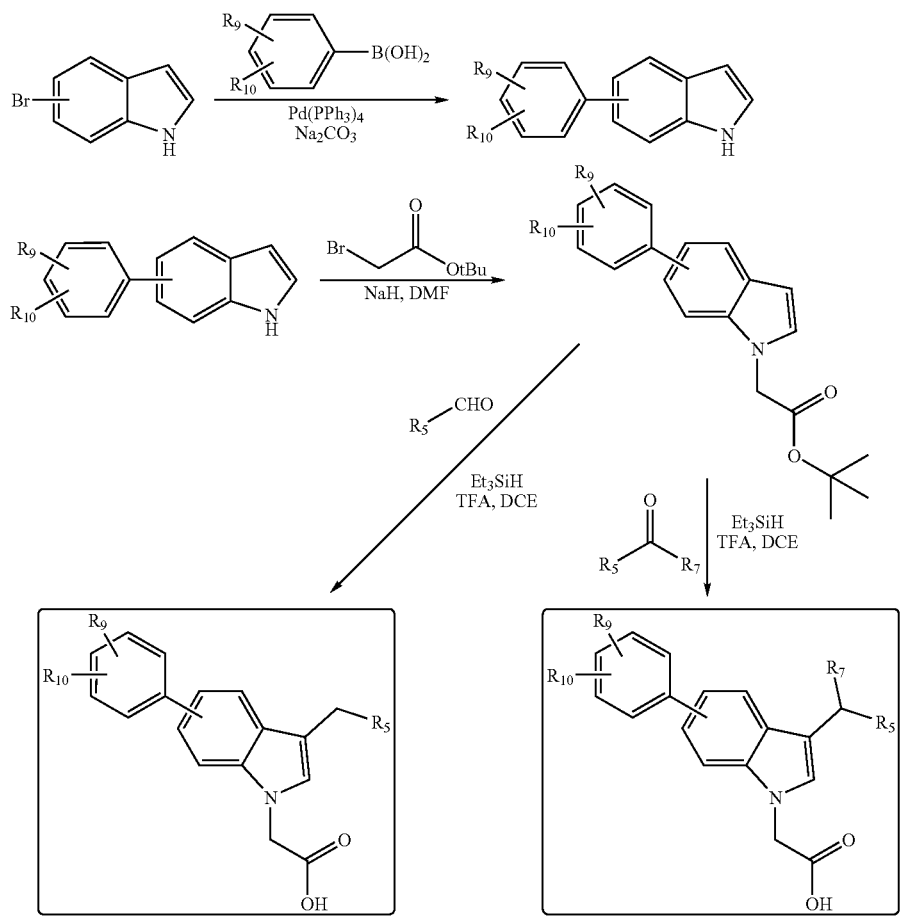

Method B

Indoles bearing alkyl, alkenyl and alkynyl substituents can also be readily prepared from indole substituted on the benzene ring with bromide, iodine, or triflate via palladium catalyzed coupling reaction with primary acetylenes. This reaction can be performed using a palladium catalyst, such as Pd(PPh$_3$)$_4$, a base, such as HN(i-Pr)$_2$ or EtN(i-Pr)$_2$, with or without a copper salt, such as CuI or CuBr, in an inert solvent, such as MeCN or toluene. The resulting alkynylindoles can be reduced to alkenyl- or alkylindoles by catalytic hydrogenation. Indoles substituted with alkyl, cycloalkyl, and benzyl groups can be prepared from the same substituted indoles by a nickle catalyzed coupling reaction. This reaction uses an alkylmagnesium coupling partner, such as C$_6$H$_{11}$,CH$_2$MgCl, PhCH$_2$MgCl, or PhCMe$_2$CH$_2$MgCl and a nickle catalyst, such as Ni(dppf)Cl$_2$ (dppf=1,1'-bis(diphenylphosphino)ferrocene) to give the corresponding substituted indoles. These indoles can then be further elaborated as described in Method A to give the desired indol-1-yl acetic acids.

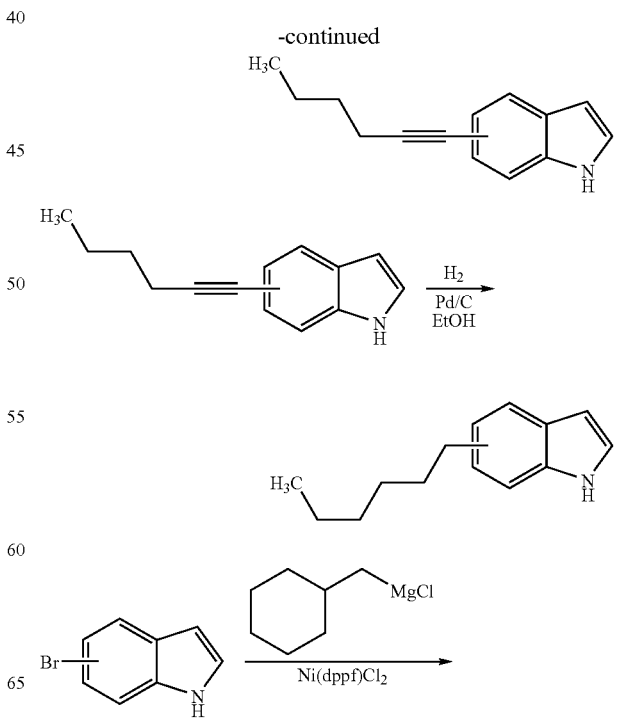

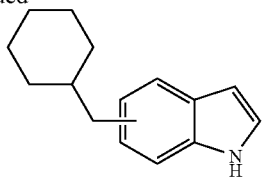

This invention also provides pharmaceutical compositions comprising the compounds of formula I either alone or in combination with excipients (i.e. pharmaceutically acceptable materials with no pharmacological effects). Such compositions for treating conditions resulting from fibrinolytic disorder such as deep vein thrombosis and coronary heart disease, pulmonary fibrosis, etc.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure, stroke, peripheral arterial occlusion, and related disease states). These measures will slow the rate of progress of the disease state and assist the body in reversing the process direction in a natural manner.

Any suitable carrier known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid, which is in admixture with the finely divided active ingredient. In tablets, the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions, which are sterile solutions or suspensions, can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physicians direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patients recovery rate. By initiating the treatment regimen with a minimal daily dose of about one gram, the blood levels of PAI-1 and the patients symptomatic relief analysis may be used to determine whether a larger dose is indicated. Based upon the data presented below, the projected daily dose for both human and veterinary use will be from about 25 to about 200 milligrams/kilogram per day, and more usually, from about 50 to about 100 milligrams/kilogram per day.

The ability of the compounds of this invention to inhibit Plasminogen Activator Inhibitor-1 was established by the following experimental procedures:

Primary Screen for the PAI-1 Inhibition

Test compounds were dissolved in DMSO at a final concentration of 10 mM, then diluted 100× in physiologic buffer. The inhibitory assay was initiated by the addition of the test compound (1-100 µM final concentration, maximum DMSO concentration of 0.2%) in a pH 6.6 buffer containing 140 nM recombinant human plasminogen activator inhibitor-1 (*Molecular Innovations*, Royal Oak, Mich.). Following a 1 hour incubation at room temperature, 70 nM of recombinant human tissue plasminogen activator (tPA) was added, and the combination of the test compound, PAI-1 and tPA was incubated for an additional 30 minutes. Following the second incubation, Spectrozyme-tPA (*American Diagnostica*, Greenwich, Conn.), a chromogenic substrate for tPA, was added and absorbance read at 405 nm at 0 and 60 minutes. Relative PAI-1 inhibition is equal to the residual tPA activity in the presence of test compound and PAI-1. Control treatments included the complete inhibition of tPA by PAI-1 at the molar ratio employed (2:1), and the absence of any effect of the test compound on tPA alone.

Assay for Determining $IC_{50}$ of Inhibition of PAI-1

This assay was based upon the non-SDS dissociable interaction between tPA and active PAI-1. Assay plates were initially coated with human tPA (10 µg/ml). The test compounds were dissolved in DMSO at 10 mM, then diluted with physiologic buffer (pH 7.5) to a final concentration of 1-50 µM. The test compounds were incubated with human PAI-1 (50 ng/ml) for 15 minutes at room temperature. The tPA-coated plate was washed with a solution of 0.05% Tween 20 and 0.1% BSA, then the plate was blocked with a solution of 3% BSA. An aliquot of the test compound/PAI-1 solution was then added to the tPA-coated plate, incubated at room temperature for 1 hour, and washed. Active PAI-1 bound to the plate was assessed by adding an aliquot of a 1:1000 dilution of the 33B8 monoclonal antibody against human PAI-1, and incubating the plate at room temperature for 1 hour (*Molecular Innovations*, Royal Oak, Mich.). The plate was again washed, and a solution of goat anti-mouse IgG-alkaline phosphatase conjugate was added at a 1:50,000 dilution in goat serum. The plate was incubated 30 minutes at room temperature, washed, and a solution of alkaline phosphatase substrate was added. The plate was incubated 45 minutes at room temperature, and color development was determined at $OD_{405\ nm}$. The quantitation of active PAI-1 bound to tPA at varying concentrations of the test compound was used to determine the $IC_{50}$. Results are analyzed using a logarithmic best-fit equation. The assay sensitivity was 5 ng/ml of human PAI-1 as determined from a standard curve ranging from 0-100 ng/ml.

The compounds of the present invention inhibited Plasminogen Activator Inhibitor-1 as summarized in Table I.

TABLE 1

Inhibition of Plasminogen Activator Inhibitor-I by Examples 1-12.

| Compound of Example | $IC_{50}$ (μM) Antibody | % Inhibition @ 25 μM |
|---|---|---|
| 1 | 19.23 | 48 |
| 2 | 15.06 | 31 |
| 3 | — | 100 |
| 4 | — | 35 |
| 5 | — | 47 |
| 6 | — | 49 |
| 7 | — | 47 |
| 8 | — | 64 |
| 9 | — | 26 |
| 10 | — | 48 |
| 11 | — | 26 |
| 12 | — | 48 |

EXAMPLE 1

{5-(3-Trifluoromethoxyphenyl)-3-[1-(4-trifluoromethylphenyl)-ethyl]-indol-1-yl}-acetic acid

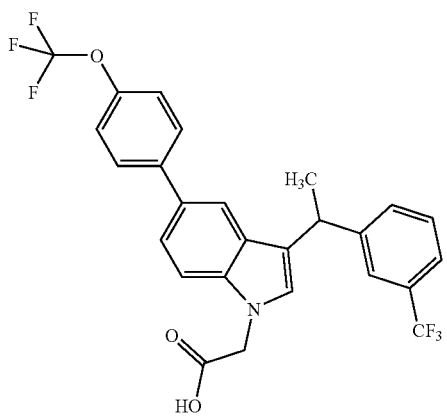

Step 1:

A solution of 9.37 g (88.4 mmol) $Na_2CO_3$ and 44 ml of water was prepared. To this solution was added 22 ml of EtOH, 4.3 g (22.1 mmol) 5-bromoindole, 5 g (24.3 mmol) 4-trifluoromethoxybenzene boronic acid, and 0.89 g (0.77 mmol) $Pd(PPh_3)_4$. The resulting mixture was heated to reflux for 8 hr. Once the mixture was cooled to room temperature, DCM was added to dissolve the solids and the resulting solution was then diluted with EtOAc, filtered through Celite®, and partitioned with water. The aqueous layer was extracted twice with EtOAc. The organic layers were combined and washed twice with brine and then dried with $MgSO_4$ and concentrated. The crude product was chromatographed on $SiO_2$ (5-20% EtOAc-Hexane) to afford 5.99 g of 5-(4-trifluoromethoxyphenyl)-1H-indole.

Step 2:

A dry 250 ml round bottom flask was charged with 72 ml anhydrous DMF, 0.38 g (9.6 mmol) NaH, and 1.99 g (7.18 mmol) 5-(4-trifluoromethoxyphenyl)-1H-indole. The solution was stirred 10 min. 1.17 ml (7.9 mmol) t-butyl bromomethyl acetate was then added and the solution was stirred for 18 hr. The solution was concentrated to afford crude [5-(4-trifluoromethoxyphenyl)-indol-1-yl]-acetic acid tert-butyl ester which was carried on directly to the next step.

Step 3:

Approximately 1.4 g (3.59 mmol) of product from Step 2 was suspended in dichloroethane (DCE). To the suspension was added 0.66 ml (4.31 mmol) 3-trifluoromethyl acetophenone and 1.72 ml (10.77 mmol) triethylsilane. The resulting solution was stirred for 30 min and then 0.83 ml (10.77 mmol) trifluoroacetic acid was added slowly. Once the addition was complete, the reaction was heated to 60° C. for 8 hr and then stirred overnight at room temperature. The solution was concentrated and the residue was purified by RP-HPLC to give 0.914 g of Example 1: mp 54-60° C.; $^1$H NMR ($CDCl_3$, 400 MHz) δ 1.74 (d, J=7.2 Hz, 3H), 4.46 (q, J=7.2 Hz, 1H), 4.91 (s, 2H), 6.93 (s,1H), 7.20-7.28 (m, 3H), 7.35-7.50 (m, 7H), 7.59 (s, 1H); MS: m/z (ESI) 506.1 (M−H); Anal. Calculated for ($C_{26}H_{19}F_6NO_3$) C, H, N.

The compounds of examples 2, 3 and 4 were prepared by the same steps using 5-bromoindole, 4-trifluoromethoxybenzene boronic acid, 2,4-dichlorobenzene boronic acid, 3-trifluoromethylbenzene boronic acid, and 3,5-bis(trifluoromethyl)benzaldehyde.

EXAMPLE 2

{3-[3,5-bis(trifluoromethyl)benzyl]-5-[4-(trifluoromethoxy)phenyl]-1H-indol-1-yl}acetic) acid

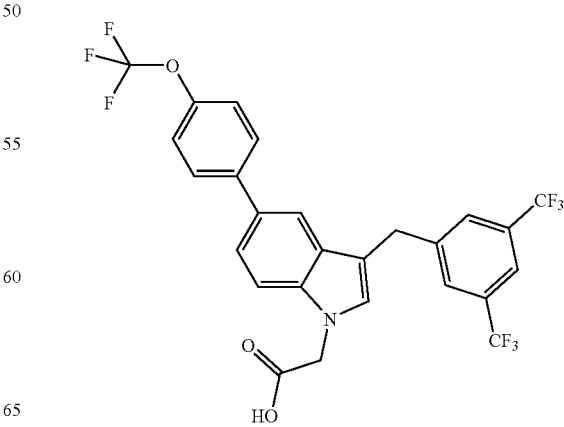

mp 188-190° C.; $^1$H NMR (CDCl$_3$, 400 MHz) δ4.26 (s, 2H), 4.91 (s, 2H), 6.85 (s, 1H), 7.25-7.30 (m, 2H), 7.31 (d, J=8.6 Hz, 1H), 7.45 (dd, J=8.5, 1.7 Hz, 1H), 7.55-7.60 (m, 2H), 7.6 (s, 1H), 7.75 (s, 3H); MS: m/z (ESI) 560.1 (M−H); Anal. calculated for (C$_{26}$H$_{16}$F$_9$NO$_3$) C, H, N.

EXAMPLE 3

[3-[3,5-bis(trifluoromethyl)benzyl]-5-(2,4-dichlorophenyl)-1H-indol-1-yl]acetic acid

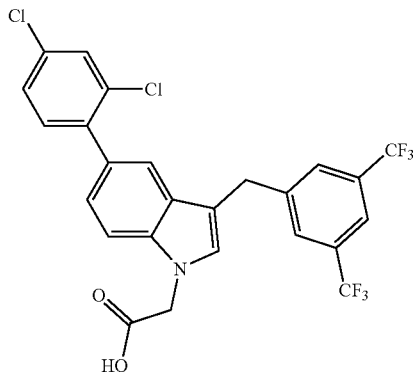

mp 150-155° C.; $^1$H NMR (CDCl$_3$, 400 MHz) δ4.27 (s, 2H), 4.91 (s, 2H), 6.86 (s, 1H), 7.33 (d, J=8.4 Hz, 1H), 7.48-7.60 (m, 3H), 7.64 (s, 1H), 7.70-7.80 (m, 5H); MS: m/z (ESI) 544.1 (M−H); Anal. calculated for (C$_{26}$H$_{16}$F$_9$NO$_2$) C, H, N.

EXAMPLE 4

{3-[3,5-bis(trifluoromethyl)benzyl]-5-[3-(trifluoromethyl)phenyl]-1H-indol-1-yl}acetic acid

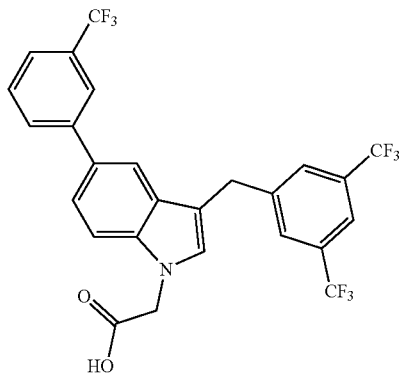

mp 175-176° C.; $^1$H NMR (CDCl$_3$, 400 MHz) δ 4.23 (s, 2H), 4.90 (s, 2H), 6.87 (s, 1H), 7.25-7.28 (m, 4H), 7.47 (s, 2H), 7.73 (s, 3H); MS: m/z (ESI) 544.0 (M−H); Anal. calculated for (C$_{25}$H$_{15}$Cl$_2$F$_6$NO$_2$) C, H, N.

EXAMPLE 5

{5-(3-chlorophenyl)-3-[1-(2-thienyl)ethyl]-1H-indol-1-yl}acetic acid

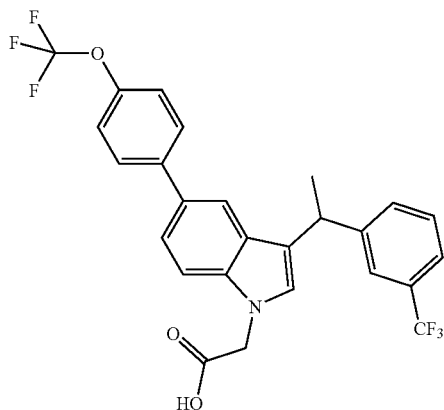

Step 1:

A solution of 9.37 g (88.4 mmol) Na$_2$CO$_3$ and 44 ml of water was prepared. To this solution was added 22 ml of EtOH, 4.3 g (22.1 mmol) 5-bromoindole, 5 g (24.3 mmol) 4-trifluoromethoxyphenyl boronic acid, and 0.89 g (0.77 mmol) Pd(PPh$_3$)$_4$. The resulting mixture was heated to reflux for 8 hr. Once the mixture was cooled to room temperature, DCM was added to dissolve the solids and the resulting solution was then diluted with EtOAc, filtered through celite, and partitioned with water. The aqueous layer was extracted twice with EtOAc. The organic layers were combined and washed twice with brine and then dried with MgSO$_4$ and concentrated. The crude product was chromatographed on SiO$_2$ (5-20% EtOAc-Hexane). The solvent was concentrated in vacuo. The residue was crystallized from ether/hexane to afford 2.38 g of 5-(3-chlorophenyl)-1H-indole.

Step 2:

A dry 500 ml Syncore flask was charged with 50 ml anhydrous DMF, 0.25 g (6.25 mmol) NaH, and 1.135 g (5.0 mmol) 5-(3-chlorophenyl)-1H-indole. The solution was stirred 10 min. 0.998 ml (7.5 mmol) t-butyl bromomethyl acetate was then added and the solution was stirred for 18 hr. The solution was concentrated under vacuum with heating to afford crude [5-(3-chlorophenyl)-indol-1-yl]-acetic acid tert-butyl ester which was carried on directly to the next step.

Step 3:

Approximately 53.3 mg (0.156 mmol) of product from Step 2 was suspended in dichloroethane (DCE). To the suspension was added 0.045 ml (0.417 mmol) 2-acetylthiophene and 0.2 ml (1.25 mmol) triethylsilane. The resulting solution was stirred for 30 min and then 0.16 ml (2.07 mmol) trifluoroacetic acid was added slowly. Once the addition was complete, the reaction was heated to 60° C. for 18 hours. The solution was concentrated and the residue was purified by RP-HPLC to give 6.2 mg of Example 5.

Examples 6-12 were synthesized using the procedure outlined for the preparation of Example 5 using 3-(trifluoromethy) phenyl boronic acid, 2,6-dichlorophenyl boronic acid, acetophenone, 2-acetylthiophene, cyclohexylmethylketone, 4-isopropylbenzaldehyde, and 4-methyl-2-pentanone.

EXAMPLE 6

[3-(1-Phenyl-ethyl)-5-(3-trifluoromethyl-phenyl)-indol-1-yl]acetic acid

EXAMPLE 7

[3-(1-Thiophen-2-yl-ethyl)-5-(3-trifluoromethyl-phenyl)-indol-1-yl]acetic acid

EXAMPLE 8

[3-(1-Cyclohexyl-ethyl)-5-(3-trifluoromethyl-phenyl)-indol-1-yl]acetic acid

EXAMPLE 9

[3-(4-Isopropyl-benzyl)-5-(3-trifluoromethyl-phenyl)-indol-1-yl]acetic acid

EXAMPLE 10

[5-(2,4-Dichloro-phenyl)-3-(1,3-dimethyl-butyl)-indol-1-yl]-acetic acid

EXAMPLE 11

[5-(2,4-Dichloro-phenyl)-3-(1-phenyl-ethyl)-indol-1-yl]-acetic acid

EXAMPLE 12

[3-(1-Cyclohelxy-ethyl)-5-(2,4-dichloro-phenyl)-indol-1-yl]-acetic acid

TABLE 2

(LCMS² Data: Molecular ion and retention time)

| $R_1$ | $R_2$ | $R_3$ | |
|---|---|---|---|
| 3-chloro | thiophene | $CH_3$ | Example 5 394 (M + H); 3.75 min |
| 3-trifluoromethyl | phenyl | $CH_3$ | Example 6 422 (M + H); 3.77 min |
| 3-trifluoromethyl | thiophene | $CH_3$ | Example 7 428 (M + H); 3.72 min |
| 3-trifluoromethyl | cyclohexyl | $CH_3$ | Example 8 428 (M + H); 4.15 min |
| 3-trifluoromethyl | 4-isopropylphenyl | H | Example 9 450 (M + H); 4.02 min |
| 2,6-dichloro | 2-methylphenyl | $CH_3$ | Example 10 403 (M + H); 4.20 min |
| 2,5-dichloro | phenyl | $CH_3$ | Example 11 424 (M + H); 3.95 min |

TABLE 2-continued (LCMS² Data: Molecular ion and retention time)

| $R_1$ | $R_2$ | $R_3$ | |
|---|---|---|---|
| 2,6-dichloro | cyclohexyl | $CH_3$ | Example 12 428 (M + H); 4.37 min |

Notes:
1. Semi-Preparative RP-HPLC Conditions:
Gilson Semi-Preparative HPLC system with Unipoint Software
Column: Phenomenex C18 Luna 21.6 mm×60 mm, 5 μM; Solvent A: Water (0.02% TFA buffer); Solvent B: Acetonitrile (0.02% TFA buffer); Solvent Gradient: Time 0: 5% B; 2.5 min: 5% B; 7 min: 95% B; Hold 95% B 5 min.
Flow Rate: 22.5 mL/min The product peak was collected based on UV absorption and concentrated.
2. Analytical LCMS Conditions:
Hewlett Packard 1100 MSD with ChemStation Software
Column: YMC ODS-AM 2.0 mm×50 mm 5 μ column at 23° C.
Solvent A: Water (0.02% TFA buffer)
Solvent B: Acetonitrile (0.02% TFA buffer)
Gradient: Time 0: 5% B; 0.3 min: 5% B; 3.0 min: 90% B; Hold 95% B 2 min.
Flow rate 1.5 mL/min
Detection: 254 nm DAD; API-ES Scanning Mode Positive 150-700; Fragmentor 70 mV.

What is claimed:
1. A Compound of formula (I):

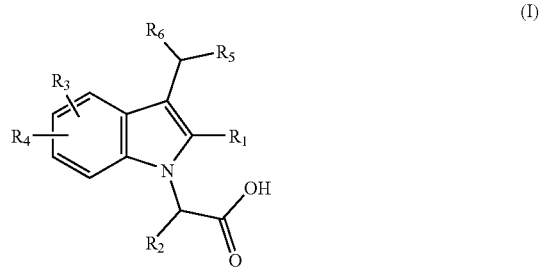

wherein:
$R_1$ is hydrogen, $C_1$-$C_6$ alkyl, $C_3$-$C_6$ cycloalkyl, —$CH_2$-$C_3$-$C_6$ cycloalkyl, or $C_1$-$C_3$ perfluoroalkyl, wherein the alkyl and cycloalkyl groups may be optionally substituted by halogen, —CN, $C_1$-$C_6$ alkoxy, —OH, —$NH_2$, or —$NO_2$;

$R_2$ is hydrogen, $C_1$-$C_8$ alkyl, $C_3$-$C_6$ cycloalkyl, —$CH_2$-$C_3$-$C_6$ cycloalkyl, thienyl, $CH_2$-thienyl, furanyl, $CH_2$-furanyl, oxazoyl, $CH_2$-oxazoyl, phenyl, benzyl, or $CH_2$-naphthyl; wherein the alkyl group and the rings of the cycloalkyl, thienyl, furanyl, oxazoyl, phenyl, benzyl, and napthyl groups may be optionally substituted by from 1 to 3 groups selected from halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —$OCHF_2$, —CN, —COOH, —$CH_2CO_2H$, —C(O)$CH_3$, —C(O)$OR_7$, —C(O)$NH_2$, —S(O)$_2CH_3$, —OH, —$NH_2$, or —$NO_2$;

$R_3$ is hydrogen, halogen, $C_1$-$C_6$ alkyl, $C_1$-$C_3$ perfluoroalkyl, $C_1$-$C_6$ alkoxy, $C_3$-$C_6$ cycloalkyl, or —$CH_2$—$C_3$-$C_6$ cycloalkyl;

$R_4$ is $C_3$-$C_8$ alkyl, $C_3$-$C_6$ cycloalkyl, —$CH_2$—$C_3$-$C_6$ cycloalkyl, thienyl, $CH_2$-thienyl, furanyl, oxazoyl, phenyl, benzo[b]furan-2-yl, benzo[b]thien-2-yl, benzo[1,3]dioxol-5-yl, or naphthyl; wherein the alkyl group and the rings of the cycloalkyl, thienyl, furanyl, oxazoyl, phenyl, benzofuranyl, benzothienyl, and napthyl groups may be optionally substituted by from 1 to 3 groups selected from halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —$OCHF_2$, —C(O)$CH_3$, —C(O)$OR_7$, —C(O)$NH_2$, —S(O)$_2CH_3$, —OH, —$NH_2$, or —$NO_2$;

$R_5$ is $C_1$-$C_8$ alkyl, $C_3$-$C_6$ cycloalkyl, —$CH_2$-$C_3$-$C_6$ cycloalkyl, pyridinyl, —$CH_2$-pyridinyl, thienyl, $CH_2$-thienyl, furanyl, $CH_2$-furanyl, oxazoyl, $CH_2$-oxazoyl, phenyl, benzyl, benzo[b]furan-2-yl, benzo[b]thien-2-yl, benzo[1,3]dioxol-5-yl, naphthyl, $CH_2$-naphyl, 9H-fluoren-1-yl, 9H-fluoren-4-yl, 9H-fluoren-9-yl, 9-fluorenone-1-yl, 9-fluorenone-2-yl, 9-fluorenone-4-yl, or $CH_2$-9H-fluoren-9-yl; wherein the alkyl group and the rings of the cycloalkyl, pyridinyl, thienyl, furanyl, oxazoyl, phenyl, benzyl, benzofuranyl, benzothienyl, napthyl, fluorenyl, and fluorenone groups may be optionally substituted by from 1 to 3 groups selected from halogen, $C_1$-$C_3$ alkyl, $C_3$-$C_6$ cycloalkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —$OCHF_2$, —CN, —COOH, —$CH_2CO_2H$, —C(O)$CH_3$, —C(O)$OR_7$, —C(O)$NH_2$, —S(O)$_2CH_3$, —OH, —$NH_2$, —$NO_2$, or phenoxy, the phenoxy group being further optionally substituted by from 1 to 3 groups selected from halogen, $C_1$-$C_3$ alkyl, or $C_1$-$C_3$ perfluoroalkyl;

$R_6$ is hydrogen, $C_1$-$C_8$ alkyl, $C_3$-$C_6$ cycloalkyl, —$CH_2$-$C_3$-$C_6$ cycloalkyl, pyridyl, thienyl, $CH_2$-thienyl, furanyl, $CH_2$-furanyl, oxazoyl, $CH_2$-oxazoyl, phenyl, benzyl, benzo[b]furan-2-yl, benzo[b]thien-2-yl, benzo[1,3]dioxol-5-yl, $CH_2$-1-naphthyl, or $CH_2$-2-naphyl; wherein the alkyl group and the rings of the cycloalkyl, thienyl, furanyl, oxazoyl, phenyl, benzyl, benzofuranyl, benzothienyl, and napthyl groups may be optionally substituted by from 1 to 3 groups selected from halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —$OCHF_2$, —CN, —COOH, —$CH_2CO_2H$, —C(O)$CH_3$, —C(O)$OR_7$, —C(O)$NH_2$, —S(O)$_2CH_3$, —OH, —$NH_2$, or —$NO_2$;

or $R_5$ and $R_6$ taken together may be $C_3$-$C_6$ cycloalkyl, 3-indan-1-yl, 1,2,3,4-tetrahydronaphthalen-1-yl, chroman-4-yl, 4H-chromen-4-yl, thiochroman-4-yl, 9H-fluoren-9-yl, 9,10-dihydroanthracen-9-yl, 9H-xanthen-9-yl, 9H-thioxanthen-9-yl, 6,7,8,9-tetrahydro-5H-benzocyclohepten-5-yl, or 10,11-dihydro-5H-dibenzo[a,d]cyclohepten-5-yl, wherein these groups may be optionally substituted by from 1 to 3 groups selected from halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —$OCHF_2$, —CN, —COOH, —$CH_2CO_2H$, —C(O)$CH_3$, —C(O)$OR_7$, —C(O)$NH_2$, —S(O)$_2CH_3$, —OH, —$NH_2$, or —$NO_2$; and $R_7$ is $C_1$-$C_6$ alkyl, $C_3$-$C_6$ cycloalkyl, —$CH_2$—$C_3$-$C_6$ cycloalkyl, or benzyl; or a pharmaceutically acceptable salt or ester form thereof.

2. The compound of claim 1 having the formula:

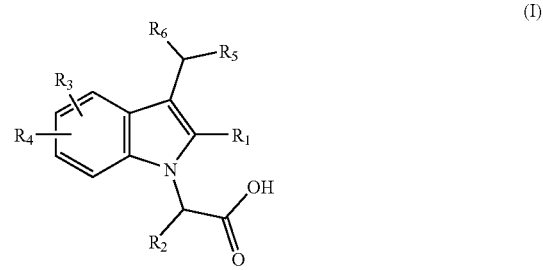

(I)

wherein $R_1$-$R_3$ and $R_5$-$R_7$ are as defined in claim 1, and $R_4$ is thienyl, furanyl, oxazoyl, phenyl, benzo[b]furan-2-yl, benzo[b]thien-$_2$-yl, benzo[1,3]dioxol-5-yl, or naphthy; wherein the rings of the thienyl, furanyl, oxazoyl, phenyl, benzofuranyl, benzothienyl, and napthyl groups may be optionally substituted by from 1 to 3 groups selected from halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —$OCHF_2$, —CN, —COOH, —$CH_2CO_2H$, —C(O)$CH_3$, —$CO_2R_7$, —C(O)$NH_2$, —S(O)$_2CH_3$, —OH, —$NH_2$, or —$NO_2$;

or a pharmaceutically acceptable salt or ester form thereof.

3. The compound of claim 1 having the formula II:

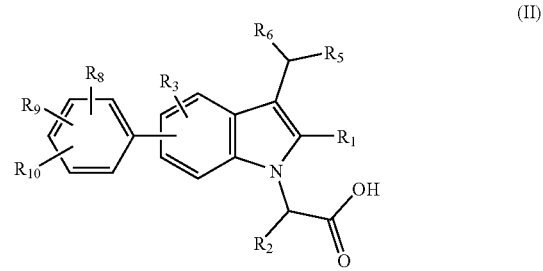

(II)

wherein:

$R_1$ is hydrogen, $C_1$-$C_6$ alkyl, $C_3$-$C_6$ cycloalkyl, —$CH_2$—$C_3$-$C_6$ cycloalkyl, or $C_1$-$C_3$ perfluoroalkyl, wherein the alkyl and cycloalkyl groups may be optionally substituted by halogen, —CN, $C_1$-$C_6$ alkoxy, —OH, —$NH_2$, or —$NO_2$;

$R_2$ is hydrogen, $C_1$-$C_8$ alkyl, $C_3$-$C_6$ cycloalkyl, or —$CH_2$-$C_3$-$C_6$ cycloalkyl, wherein the alkyl group and the rings of the cycloalkyl groups may be optionally substituted by from 1 to 3 groups selected from halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —OCHF$_2$, —CN, —COOH, —CH$_2$CO$_2$H, —C(O)CH$_3$, —C(O)OR$_7$, —C(O)NH$_2$, —S(O)$_2$CH$_3$, —OH, —NH$_2$, or —NO$_2$;

R$_3$ is hydrogen, halogen, C$_1$-C$_6$ alkyl, C$_1$-C$_3$ perfluoroalkyl, C$_1$-C$_6$ alkoxy, C$_3$-C$_6$ cycloalkyl, or —CH$_2$-C$_3$-C$_6$ cycloalkyl;

R$_5$ is C$_1$-C$_8$ alkyl, C$_3$-C$_6$ cycloalkyl, —CH$_2$—C$_3$-C$_6$ cycloalkyl, phenyl, benzyl, naphthyl, or CH$_2$-naphyl, wherein the alkyl group and the rings of the cycloalkyl, phenyl, and benzyl groups may be optionally substituted by from 1 to 3 groups selected from halogen, C$_1$-C$_3$ alkyl, C$_3$-C$_6$ cycloalkyl, C$_1$-C$_3$ perfluoroalkyl, —O—C$_1$-C$_3$ perfluoroalkyl, —S—C$_1$-C$_3$ perfluoroalkyl, C$_1$-C$_3$ alkoxy, —OCHF$_2$, —CN, —COOH, —CH$_2$CO$_2$H, —C(O)CH$_3$, —C(O)OR$_7$, —C(O)NH$_2$, —S(O)$_2$CH$_3$, —OH, —NH$_2$, —NO$_2$, or phenoxy; the phenoxy group being optionally substituted by from 1 to 3 groups selected from halogen, C$_1$-C$_3$ alkyl, or C$_1$-C$_3$ perfluoroalkyl;

R$_6$ is hydrogen, C$_1$-C$_8$ alkyl, C$_3$-C$_6$ cycloalkyl, or —CH$_2$—C$_3$-C$_6$ cycloalkyl, wherein the alkyl group and the rings of the cycloalkyl groups may be optionally substituted by from 1 to 3 groups selected from halogen, C$_1$-C$_3$ alkyl, C$_1$-C$_3$ perfluoroalkyl, —O—C$_1$—C$_3$ perfluoroalkyl, —S—C$_1$-C$_3$ perfluoroalkyl, C$_1$-C$_3$ alkoxy, —OCHF$_2$, —CN, —COOH, —CH$_2$CO$_2$H, —C(O)CH$_3$, —C(O)NH$_2$, —S(O)$_2$CH$_3$, —OH, —NH$_2$, or —NO$_2$;

or R$_5$ and R$_6$ taken together may be a C$_3$-C$_6$ cycloalkyl group optionally substituted by from 1 to 3 groups selected from halogen, C$_1$-C$_3$ alkyl, C$_1$-C$_3$ perfluoroalkyl, —O—C$_1$-C$_3$ perfluoroalkyl, —S—C$_1$-C$_3$ perfluoroalkyl, —C$_1$-C$_3$ alkoxy, —OCHF$_2$, —CN, —COOH, —CH$_2$CO$_2$H, —C(O)CH$_3$, —C(O)NH$_2$, —S(O)$_2$CH$_3$, —OH, —NH$_2$, or —NO$_2$;

R$_8$, R$_9$, R$_{10}$ are each independently hydrogen, halogen, C$_1$-C$_3$ alkyl, C$_1$-C$_3$ perfluoroalkyl, —O—C$_1$-C$_3$ perfluoroalkyl, —S—C$_1$-C$_3$ perfluoroalkyl, C$_1$—C$_3$ alkoxy, —OCHF$_2$, —C(O)CH$_3$, —C(O)OR$_7$, —C(O)NH$_2$, —S(O)$_2$CH$_3$, —OH, —NH$_2$, or —NO$_2$;

or a pharmaceutically acceptable salt or ester form thereof.

4. The compound of claim 1 having the formula III:

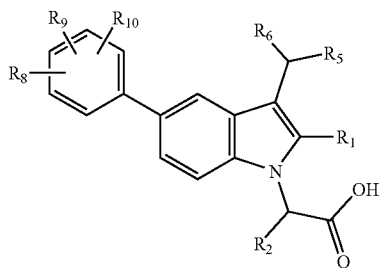

III wherein:

R$_1$ is hydrogen or C$_1$-C$_6$ alkyl;

R$_2$ is hydrogen or C$_1$-C$_3$ alkyl, optionally substituted by halogen;

R$_5$ is C$_1$-C$_8$ alkyl, C$_3$-C$_6$ cycloalkyl, —CH$_2$—C$_3$-C$_6$ cycloalkyl, phenyl, benzyl, or thienyl, wherein the alkyl group and the rings of the cycloalkyl, phenyl, thienyl and benzyl groups may be optionally substituted by from 1 to 3 groups selected from halogen, C$_1$-C$_3$ alkyl, C$_3$-C$_6$ cycloalkyl, C$_1$-C$_3$ perfluoroalkyl, —O—C$_1$-C$_3$ perfluoroalkyl, —S—C$_1$-C$_3$ perfluoroalkyl, C$_1$-C$_3$ alkoxy, —OCHF$_2$, —CN, —COOH, —CH$_2$CO$_2$H, —C(O)CH$_3$, —C(O)NH$_2$, —S(O)$_2$CH$_3$, —OH, —NH$_2$, or —NO$_2$;

R$_6$ is hydrogen or C$_1$-C$_6$ alkyl,

R$_8$, R$_9$, R$_{10}$ are each independently hydrogen, halogen, C$_1$-C$_3$ alkyl, C$_1$-C$_3$ perfluoroalkyl, —O—C$_1$-C$_3$ perfluoroalkyl, —S—C$_1$-C$_3$ perfluoroalkyl, C$_1$-C$_3$ alkoxy, —OCHF$_2$, —C(O)CH$_3$, —C(O)NH$_2$, —S(O)$_2$CH$_3$, —OH, —NH$_2$, or —NO$_2$;

or a pharmaceutically acceptable salt or ester form thereof.

5. The compound of claim 1 which is {5-(3-trifluoromethoxyphenyl)-3-[1-(4-trifluoromethylphenyl)-ethyl]-indol-1-yl}-acetic acid or a pharmaceutically acceptable salt or ester form thereof.

6. The compound of claim 1 which is {3-[3,5-bis(trifluoromethyl)benzyl]-5-[4-(trifluoromethoxy)phenyl]1H-indol-1-yl}acetic) acid or a pharmaceutically acceptable salt or ester form thereof.

7. The compound of claim 1 which is [3-[3,5-bis(trifluoromethyl)benzyl]-5-(2,4-dichlorophenyl)-1H-indol-1-yl] acetic acid or a pharmaceutically acceptable salt or ester form thereof.

8. The compound of claim 1 which is {3-[3,5bis(trifluoromethyl)benzyl]-5-[3-(trifluoromethyl)phenyl]-1H-indol-1-yl}acetic acid or a pharmaceutically acceptable salt or ester form thereof.

9. The compound of claim 1 which is {5-(3-chlorophenyl)-3-[1-(2-thienyl)ethyl]-1H-indol-1]-yl}acetic acid or a pharmaceutically acceptable salt or ester form thereof.

10. The compound of claim 1 which is [3-(1-phenylethyl)-5-(3-trifluoromethyl-phenyl)-indol-1-yl]acetic acid or a pharmaceutically acceptable salt or ester form thereof.

11. The compound of claim 1 which is [3-(1-thiophen-2yl-ethyl)-5-(3-trifluoromethyl-phenyl)-indol-1-yl]acetic acid or a pharmaceutically acceptable salt or ester form thereof.

12. The compound of claim 1 which is [3-(1-cyclohexyl-ethyl)-5-(3-trifluoromethyl-phenyl)-indol-1-yl]acetic acid or a pharmaceutically acceptable salt or ester form thereof.

13. The compound of claim 1 which is [3-(4-isopropylbenzyl)-5-(3-trifluoromethyl-phenyl)-indol-1-yl]acetic acid or a pharmaceutically acceptable salt or ester form thereof.

14. The compound of claim 1 which is [5-(2,4-dichlorophenyl)-3-(1,3-dimethyl-butyl)-indol-1-yl]-acetic acid or a pharmaceutically acceptable salt or ester form thereof.

15. The compound of claim 1 which is [5-(2,4-dichlorophenyl)-3-(1-phenyl-ethyl)-indol-1-yl]-acetic acid or a pharmaceutically acceptable salt or ester form thereof.

16. The compound of claim 1 which is [3-(1-cyclohexyl-ethyl)-5-(2,4-dichloro-phenyl)-indol-1-yl]acetic acid or a pharmaceutically acceptable salt or ester form thereof.

17. A pharmaceutical composition comprising a therapeutically effective amount of the compound of claim 1 and a pharmaceutical carrier.

18. A method for the treatment of thrombosis, fibrinolytic impairment, peripheral arterial disease, stroke associated with or resulting from atrial fibrillation, myocardial ischemia, cardiovascular disease caused by noninsulin dependent diabetes mellitus, the formation of atherosclerotic plaques, chronic obstructive pulmonary disease, renal fibrosis, polycystic ovary syndrome, Alzheimer's disease, breast cancer or ovarian cancer in a mammal, the method comprising administering to a mammal in need thereof, a therapeutically effective amount of a compound of formula I

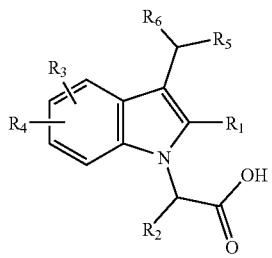

(I)

wherein:
- $R_1$ is hydrogen, $C_1$-$C_6$ alkyl, $C_3$-$C_6$ cycloalkyl, —$CH_2$—$C_3$-$C_6$ cycloalkyl, or $C_1$-$C_3$ perfluoroalkyl, wherein the alkyl and cycloalkyl groups are optionally substituted by halogen, —CN, $C_1$-$C_6$ alkoxy, —OH, —$NH_2$, or —$NO_2$;
- $R_2$ is hydrogen, $C_1$-$C_8$ alkyl, $C_3$-$C_6$ cycloalkyl, —$CH_2$—$C_3$-$C_6$ cycloalkyl, thienyl, $CH_2$-thienyl, furanyl, $CH_2$-furanyl, oxazoyl, $CH_2$-oxazoyl, phenyl, benzyl, or $CH_2$-naphthyl, wherein the alkyl group and the rings of the cycloalkyl, thienyl, furanyl, oxazoyl, phenyl, benzyl, and naphthyl groups are optionally substituted by from 1 to 3 groups selected from alogen, $C_1$-$C_3$ alkyl, $C_1$-$C_3$ perfluoroalkyl, —O—$C_{1\text{-}C3}$ perfluoroalkyl, —S—$C_1$-$C_3$ perfluoroalkyl, $C_1$-$C_3$ alkoxy, —$OCHF_2$, —CN, —COOH, —$CH_2CO_2H$, —$C(O)CH_3$, —$C(O)OR_7$, —$C(O)NH_2$, —$S(O)_2CH_3$, —OH, —$NH_2$, or —$NO_2$;
- $R_3$ is hydrogen, halogen, $C_1$-$C_6$ alkyl, $C_1$-$C_3$ perfluoroalkyl, $C_1$-$C_6$ alkoxy, $C_3$-$C_6$ cycloalkyl, or —$CH_2$—$C_3$-$C_6$ cycloalkyl;
- $R_4$ is $C_3$-$C_8$ alkyl, $C_3$-$C_6$ cycloalkyl, —$CH_2$—$C_3$-$C_6$ cycloalkyl, thienyl, $CH_2$-thienyl, furanyl, oxazoyl, phenyl, benzo[b]furan-2-yl, benzo[b]thien-2-yl, benzo[1,3]dioxol-5-yl, or naphthyl, wherein the alkyl group and the rings of the cycloalkyl, thienyl, furanyl, oxazoyl, phenyl, benzofuranyl, benzothienyl, and naphthyl groups are optionally substituted by from 1 to 3 groups selected from halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —$OCHF_2$, —$C(O)CH_3$, —$C(O)OR_7$, —$C(O)NH_2$, —$S(O)_2CH_3$, —OH, —$NH_2$, or —$NO_2$;
- $R_5$ is $C_1$-$C_8$ alkyl, $C_3$-$C_6$ cycloalkyl, —$CH_2$—$C_3$-$C_6$ cycloalkyl, pyridinyl, —$CH_2$-pyridinyl, thienyl, $CH_2$-thienyl, furanyl, $CH_2$-furanyl, oxazoyl, $CH_2$-oxazoyl, phenyl, benzyl, benzo[b]furan-2-yl, benzo[b]thien-2-yl, benzo[1,3]dioxol-5-yl, naphthyl, $CH_2$-naphyl, 9H-fluoren-1-yl, 9H-fluoren-4-yl, 9H-fluoren-9-yl, 9-fluorenone-1-yl, 9-fluorenone-2-yl, 9fluorenone-4-yl, or $CH_2$-9H-fluoren-9-yl, wherein the alkyl group and the rings of the cycloalkyl, pyridinyl, thienyl, furanyl, oxazoyl, phenyl, benzyl, benzofuranyl, benzothienyl, naphthyl, fluorenyl, and fluorenone groups are optionally substituted by from 1 to 3 groups selected from halogen, $C_1$-$C_3$ alkyl, $C_3$-$C_6$ cycloalkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, phenoxy, —$OCHF_2$, —CN, —COOH, —$CH_2CO_2H$, —$C(O)CH_3$, —$C(O)OR_7$, —$C(O)NH_2$, —$S(O)_2CH_3$, —OH, —$NH_2$, or —$NO_2$, wherein the phenoxy group is optionally substituted by from 1 to 3 groups selected from halogen, $C_1$-$C_3$ alkyl, or $C_1$-$C_3$ perfluoroalkyl;
- $R_6$ is hydrogen, $C_1$-$C_8$ alkyl, $C_3$-$C_6$ cycloalkyl, —$CH_2$—$C_3$-$C_6$ cycloalkyl, pyridyl, thienyl, $CH_2$-thienyl, furanyl, $CH_2$-furanyl, oxazoyl, $CH_2$-oxazoyl, phenyl, benzyl, benzo[b]furan-2-yl, benzo [b]thien2-yl, benzo1,3]dioxol-5-yl, $CH_2$-1-naphthyl, or $CH_2$-2-naphyl, wherein the alkyl group and the rings of the cycloalkyl, thienyl, furanyl, oxazoyl, phenyl, benzyl, benzofuranyl, benzothienyl, and naphthyl groups are optionally substituted by from 1 to 3 groups selected from halogen, $C_1$-$C_3$ alkyl, $C_{1\text{-}C3}$ perfluoroalkyl, —O—$C_1$-$C_3$ perfluoroalkyl, —S—$C_1$-$C_3$ perfluoroalkyl, $C_1$-$C_3$ alkoxy, —$OCHF_2$, —CN, —COOH, —$CH_2CO_2H$, —$C(O)CH_3$, —$C(O)OR_7$, —$C(O)NH_2$, —$S(O)_2CH_3$, —OH, —$NH_2$, or —$NO_2$;
- or $R_5$ and $R_6$ taken together may be $C_3$-$C_6$ cycloalkyl, 3-indan-1-yl, 1,2,3,4-tetrahydronaphthalen-1-yl, chroman-4-yl, 4H-chromen-4-yl, thiochroman-4-yl, 9H-fluoren-9-yl, 9,10-dihydroanthracen-9-yl, 9H-xanthen-9-yl, 9H-thioxanthen-9-yl, 6,7,8,9-tetrahydro-5H-benzocyclohepten-5-yl, or 10,11-dihydro-5H-dibenzo[a,d]cyclohepten-5-yl, wherein these groups are optionally substituted by from 1 to 3 groups selected from halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —$OCHF_2$, —CN, —COOH, —$CH_2CO_2H$, —$C(O)CH_3$, —$C(O)OR_7$, —$C(O)NH_2$, —$S(O)_2CH_3$, —OH, —$NH_2$, or —$NO_2$; and
- $R_7$ is $C_1$-$C_6$ alkyl, $C_3$-$C_6$ cycloalkyl, —$CH_2$-$C_3$—$C_6$ cycloalkyl, or benzyl;

or a pharmaceutically acceptable salt or ester form thereof.

19. A method of claim 18 wherein the thrombosis or fibrinolytic impairment is associated with formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery or peripheral arterial occlusion.

20. The method of claim 18 wherein said method is for the treatment of peripheral arterial disease in a mammal.

21. The method of claim 18 wherein said method is for the treatment of stroke associated with or resulting from atrial fibrillation in a mammal.

22. The method of claim 18 wherein said method is for the treatment of deep vein thrombosis in a mammal.

23. The method of claim 18 wherein said method is for the treatment of myocardial ischemia in a mammal.

24. The method of claim 18 wherein said method is for the treatment of cardiovascular disease caused by noninsulin dependent diabetes mellitus in a mammal.

25. The method of claim 18 wherein said method is for the treatment of the formation of atherosclerotic plaques in a mammal.

26. The method of claim 18 wherein said method is for the treatment of chronic obstructive pulmonary disease in a mammal.

27. The method of claim 18 wherein said method is for the treatment of renal fibrosis in a mammal.

28. The method of claim 18 wherein said method is for the treatment of polycystic ovary syndrome in a mammal.

29. The method of claim 18 wherein said method is for the treatment of Alzheimer's disease in a mammal.

30. The method of claim 18 wherein said method is for the treatment of breast or ovarian cancer in a mammal, comprising administering to a mammal in need thereof a pharmaceutically effective amount of a compound of claim 1.

31. The compound of claim 1 wherein $R_4$ is phenyl, wherein the rings of the phenyl group are optionally substituted by from 1 to 3 groups selected from halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —OCHF$_2$, —C(O)CH$_3$, —C(O)OR$_7$, —C(O)NH$_2$, —S(O)$_2$CH$_3$, —OH, —NH$_2$, or —NO$_2$.

32. The compound of claim 3 wherein at least one of $R_8$, $R_9$, $R_{10}$ is independently halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —OCHF$_2$, —C(O)CH$_3$, —C(O)OR$_7$, —C(O)NH$_2$, —S(O)—$_2$CH$_3$, —OH, —NH$_2$, or —NO$_2$.

33. The compound of claim 32 wherein $R_5$ is $C_1$-$C_8$ alkyl, $C_3$-$C_6$ cycloalkyl, or —CH$_2$—$C_3$-$C_6$ cycloalkyl, wherein the alkyl group and the rings of the cycloalkyl group are optionally substituted by from 1 to 3 groups selected from halogen, $C_1$-$C_3$ alkyl, $C_3$-$C_6$ cycloalkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —OCHF$_2$, —CN, —COOH, —CH$_2$CO$_2$H, —C(O)CH$_3$, —C(O)OR$_7$, —C(O)NH$_2$, —S(O)$_2$CH$_3$, —OH, —NH$_2$, —NO$_2$, or phenoxy; the phenoxy group being optionally substituted by from 1 to 3 groups selected from halogen, $C_1$-$C_3$ alkyl, or $C_1$-$C_3$ perfluoroalkyl.

34. The compound of claim 4 wherein at least one of $R_8$, $R_9$, $R_{10}$ is independently halogen, $C_1$-$C_3$ alkyl, $C_1$—$C_3$ perfluoroalkyl, —O—$C_1$-$C_3$ perfluoroalkyl, —S—$C_1$-$C_3$ perfluoroalkyl, $C_1$-$C_3$ alkoxy, —OCHF$_2$, —C(O)CH$_3$, —C(O)OR$_7$, —C(O)NH$_2$, —S(O)—$_2$CH$_3$, —OH, —NH$_2$, or —NO$_2$.

35. The compound of claim 34 wherein $R_5$ is $C_1$-$C_8$ alkyl, $C_3$-$C_6$ cycloalkyl, or —CH$_2$-$C_3$-$C_6$ cycloalkyl, wherein the alkyl group and the rings of the cycloalkyl group are optionally substituted by from 1 to 3 groups selected from halogen, $C_1$-$C_3$ alkyl, $C_3$-$C_6$ cycloalkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —OCHF$_2$, —CN, —COOH, —CH$_2$CO$_2$H, —C(O)CH$_3$, —C(O)OR$_7$, —C(O)NH$_2$, —S(O)$_2$CH$_3$, —OH, —NH$_2$, —NO$_2$, or phenoxy; the phenoxy group being optionally substituted by from 1 to 3 groups selected from halogen, $C_1$-$C_3$ alkyl, or $C_1$-$C_3$ perfluoroalkyl.

36. The method of claim 18 wherein $R_4$ is phenyl, wherein the rings of the phenyl group are optionally substituted by from 1 to 3 groups selected from halogen, $C_1$-$C_3$ alkyl, $C_1$-$C_3$ perfluoroalkyl, —O—$C_{1-C3}$ perfluoroalkyl, —S—$C_1$-$C_3$ perfluoroalkyl, $C_1$-$C_3$ alkoxy, —OCHF$_2$, —C(O)CH$_3$, —C(O)OR$_7$, —C(O)NH$_2$, —S(O)$_2$CH$_3$, —OH, —NH$_2$, or —NO$_2$.

37. The method of claim 18 wherein the compound has the compound of formula III:

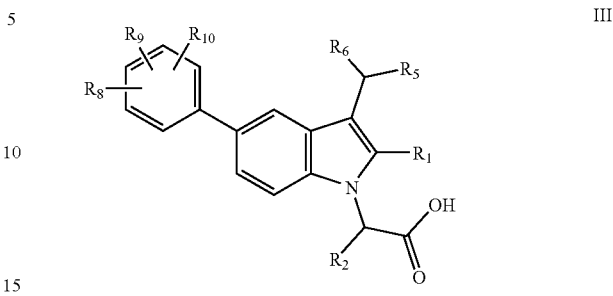

wherein:

$R_1$ is hydrogen or $C_1$-$C_6$ alkyl;

$R_2$ is hydrogen or $C_1$-$C_3$ alkyl, optionally substituted by halogen;

$R_5$ is $C_1$-$C_8$ alkyl, $C_3$-$C_6$ cycloalkyl, —CH$_2$-$C_3$-$C_6$ cycloalkyl, phenyl, benzyl, or thienyl, wherein the alkyl group and the rings of the cycloalkyl, phenyl, thienyl and benzyl groups may be optionally substituted by from $_1$ to $_3$ groups selected from halogen, $C_1$-$C_3$ alkyl, $C_3$-$C_6$ cycloalkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —OCHF$_2$, —CN, —COOH, —CH$_2$CO$_2$H, —C(O)CH$_3$, —C(O)NH$_2$, —S(O)$_2$CH$_3$, —OH, —NH$_2$, or —NO$_2$;

$R_6$ is hydrogen or $C_1$-$C_6$ alkyl, $R_8$, $R_9$, $R_{10}$ are each independently hydrogen, halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —OCHF$_2$, —C(O)CH$_3$, —C(O)NH$_2$, —S(O)$_2$CH$_3$, —OH, —NH$_2$, or —NO$_2$;

or a pharmaceutically acceptable salt or ester form thereof.

38. The method of claim 37 wherein $R_5$ is $C_1$-$C_8$ alkyl, $C_3$-$C_6$ cycloalkyl, or —CH$_2$—$C_3$-$C_6$ cycloalkyl, wherein the alkyl group and the rings of the cycloalkyl group are optionally substituted by from 1 to 3 groups selected from halogen, $C_1$-$C_3$ alkyl, $C_3$-$C_6$ cycloalkyl, $C_1$—$C_3$ perfluoroalkyl, —O—$C_1$-$C_3$ perfluoroalkyl, —S—$C_1$-$C_3$ perfluoroalkyl, $C_1$-$C_3$ alkoxy, —OCHF$_2$, —CN, —COGH, —CH$_2$CO$_2$H, —C(O)CH$_3$, —C(O)NH$_2$, —S(O)$_2$CH$_3$, —OH, —NH$_2$, or —NO$_2$.

* * * * *